(12) United States Patent
Gomi et al.

(10) Patent No.: US 8,450,101 B2
(45) Date of Patent: May 28, 2013

(54) REACTION CHIP, REACTION METHOD, TEMPERATURE CONTROLLING UNIT FOR GENE TREATING APPARATUS AND GENE TREATING APPARATUS

(75) Inventors: Sayaka Gomi, Tokyo (JP); Shuichi Akashi, Tokyo (JP); Daisuke Numai, Tokyo (JP); Ryoko Imagawa, Tokyo (JP); Masaaki Chino, Tokyo (JP); Eiji Kawata, Tokyo (JP); Masahiko Amano, Tokyo (JP)

(73) Assignee: Toppan Printing Co., Ltd. (JP)

( * ) Notice: Subject to any disclaimer, the term of this patent is extended or adjusted under 35 U.S.C. 154(b) by 307 days.

(21) Appl. No.: 12/799,410

(22) Filed: Apr. 22, 2010

(65) Prior Publication Data

US 2010/0216193 A1 Aug. 26, 2010

Related U.S. Application Data

(63) Continuation of application No. PCT/JP2008/069273, filed on Oct. 23, 2008.

(30) Foreign Application Priority Data

Oct. 26, 2007 (JP) ................................. 2007-279107
Oct. 26, 2007 (JP) ................................. 2007-279108
Oct. 26, 2007 (JP) ................................. 2007-279109

(51) Int. Cl.
*C12M 1/00* (2006.01)
*C12M 1/36* (2006.01)
*G01N 21/00* (2006.01)

(52) U.S. Cl.
USPC ................. 435/283.1; 435/287.2; 435/288.7; 422/68.1; 422/82.05; 422/82.12; 422/109

(58) Field of Classification Search
None
See application file for complete search history.

(56) References Cited

U.S. PATENT DOCUMENTS

2005/0123457 A1* 6/2005 Tajima et al. ................. 422/130
2005/0153430 A1* 7/2005 Ohtaka ....................... 435/287.2

FOREIGN PATENT DOCUMENTS

| JP | 9119928 | 5/1997 |
|----|---------|--------|
| JP | 9257748 | 10/1997 |
| JP | 9313163 | 12/1997 |
| JP | 9322755 | 12/1997 |
| JP | 2000316561 | 11/2000 |
| JP | 2002503336 | 1/2002 |
| JP | 2002505946 | 2/2002 |
| JP | 2002300894 | 10/2002 |
| JP | 2004502164 | 1/2004 |
| JP | 2006238848 | 9/2006 |
| JP | 2006275723 | 10/2006 |
| JP | 2007090290 | 4/2007 |
| WO | WO 02/01180 | 1/2002 |
| WO | 2006069757 | 7/2006 |
| WO | 2006098435 | 9/2006 |

* cited by examiner

*Primary Examiner* — Betty Forman
(74) *Attorney, Agent, or Firm* — Squire Sanders (US) LLP

(57) ABSTRACT

The reaction chip of the present invention has a plurality of recesses 6 constituting a part of a reaction container and a groove constituting a part of a channel formed on at least one of one face of a first base material (resin base material 2) and one face of a second base material (metallic base material) and a notch 15 showing a gradual increase in width and a gradual increase in depth from one face 2*d* of the base material toward an inner wall surface 6*d* of the recess is formed on an edge of at least one recess in an extending direction of the groove. One face of the first base material and one face of the second base material are stuck together opposite to each other to form the plurality of reaction containers and the channel.

3 Claims, 43 Drawing Sheets
(2 of 43 Drawing Sheet(s) Filed in Color)

REACTION CHIP, REACTION METHOD, TEMPERATURE CONTROLLING UNIT FOR GENE TREATING APPARATUS AND GENE TREATING APPARATUS

BACKGROUND OF THE INVENTION

1. Field of the Invention

The present invention relates to a reaction chip and a reaction method suitably used for a biochemical reaction such as a chemical reaction, DNA reaction, and protein reaction and a temperature controlling unit and a gene treating apparatus including the temperature controlling unit for treatment such as amplification on genes contained in a biological sample.

2. Description of the Related Art

In recent years, in the field of, for example, a biochemical reaction such as a chemical reaction, DNA reaction, and protein reaction, a technology called a μ-TAS (Total Analysis System) or Lab-on-Chip is studied and put to practical use as a technique to treat a very small quantity of sample solution on a chip. This enables a reaction experiment, which required large-scale laboratory equipment and a large quantity of reaction reagents in the past, to perform with a small quantity of reaction reagents using a reaction chip measuring several mm or less pre side.

Examples of this kind of biochemical reaction include a DNA amplification reaction by an enzyme reaction, hybridization reaction to detect a sequence of specimen DNA by using a probe DNA having a known sequence, and detection reaction of SNP (monobasic polymorphism) in a DNA sequence. The invader (registered trademark) method and the TaqMan PCR method are known as SNP detection methods (see, for example, Patent Document 1).

When these reactions are caused using a chip, for example, to decide the sequence of a gene or DNA, a method by which a probe DNA is fixed onto slide glass to allow a hybridization reaction thereon is known.

Further, a method by which a microscopic hole or dent called a well is formed on a chip to use the well as a reaction field is known.

A plurality of well-shaped reaction containers is mutually connected by a reagent solution channel installed from a reagent reservoir part (see, for example, Patent Document 2). When a reagent solution is fed by using such a channel, it is important to fill a reaction container with the reagent solution to prevent bubbles from being left behind. If bubbles remain inside the reaction container, quantities and concentrations of the reagent solution in each reaction container fluctuate, leading to fluctuations of reaction states. Moreover, even if reaction states do not fluctuate, it is extremely probable that an error of photometric intensity is caused by the bubbles.

Thus, several methods are proposed to remove bubbles from the reaction container.

As a method thereof, a liquid circuit having at least one channel inside a layered product formed by laminating a plurality of substrates in which a communication hole communicating the channel and outside by passing through at least one substrate is proposed (see, for example, Patent Document 3). Patent Document 3 discloses that the communication hole is a hole formed in a single-crystal silicon substrate or glass substrate by using photolithography and has a tapered inner circumferential surface with an increasingly smaller opening area from the channel toward the outside to remove bubbles to the outside through the communication hole. Further, the communication hole preferably has at least hydrophobicity and Patent Document 3 describes for this purpose that the substrate itself has hydrophobicity or adding hydrophobicity to a substrate having no hydrophobicity afterwards.

Further, a reaction chip having a channel passing through a first surface and a second surface and including a bubble trap to separate bubbles fed together with a sample in each sample hole is proposed (see, for example, Patent Document 4).

Incidentally, a reagent solution fed to a chip used for reaction analysis is frequently a reagent solution having high viscosity such as organic substance for a chemical reaction and extracted DNA, synthetic DNA, and enzyme for a biochemical reaction. When using such a reagent solution, according to the method described in Patent Document 2 or 3, there is a possibility that bubbles are not sufficiently removed or separated so that bubbles remain in the reaction container. Moreover, the method described in Patent Document 2 or 3 is a technology applicable only to a so-called open reaction container that is open to the outer space and is not applicable to a closed reaction container whose outer circumference is completely enclosed by walls.

In addition, a method of making a reaction container hydrophobic with surface treatment such as corona treatment and plasma treatment is frequently used to remove bubbles. In this case, however, surface modification of the reaction container may occur to result in different batch reaction conditions such as a change in pH, posing a problem of a possibility of an intended desired reaction from being blocked. Moreover, if plasma treatment is applied, surface modification of the reaction container occurs, but the surface modification is hard to persist so that there is a problem that the state immediately after treatment cannot be maintained.

When a reaction is caused using these analysis chips, a reaction reagent is first arranged inside a plurality of well-shaped reaction containers. Next, a reaction reagent solution is fed to the plurality of well-shaped reaction containers via a channel by infusing the reaction reagent solution into the analysis chip. Accordingly, the fixing reagent and the reaction reagent solution come into contact to start a reaction. The well-shaped reaction containers are heated during reaction if necessary.

However, according to the above reaction method, when the reaction reagent solution is fed into the well-shaped reaction container via the channel, there is a possibility that the fixing reagent prearranged inside the well-shaped reaction container flows out to adjacent well-shaped reaction containers. Accordingly, there is a problem that contamination may be caused. There is also a possibility that the fixing reagent, reaction reagent solution, or fluorescent substance for detection is diffused into the adjacent well-shaped reaction containers during reaction in each well-shaped reaction container. Accordingly, there is a problem that it becomes impossible to measure accurate reaction data.

Thus, a reaction chip and a reaction method capable of preventing an occurrence of such contamination and measuring accurate reaction data are disclosed (see, for example, Patent Document 5).

The reaction chip described in Patent Document 5 is constituted by a substrate forming a well-shaped reaction container and a cover material covering the substrate. The reaction method using the reaction chip is to cover a reaction reagent arranged in the well-shaped reaction container with a hot-melt sealing compound and feed the reaction reagent solution on top of the sealing compound before the sealing compound being melted by heating to bring the reaction reagent and the reaction reagent solution into contact.

According to the method, the reaction reagent will not flow out to adjacent well-shaped reaction containers, so that contamination can be prevented from occurring.

For a reaction chip used for biochemical reaction such as an enzyme reaction, it is advantageous to use a substrate with a high thermal conductivity because such a reaction frequently requires heating a reagent. However, if a reaction reagent is fixed onto a substrate with a high thermal conductivity, heat when the substrate and cover material were stuck together may be conducted to the reaction reagent, posing a problem that activity of the reaction reagent is lowered or devitalized. Speaking of, for example, the reaction method described in Patent Document 5, it is desirable to use a substrate with a high thermal conductivity as a substrate on the side on which a well-shaped reaction container is formed, but in such a case, the above problem is caused.

If a reaction reagent is fixed onto a substrate with a high thermal conductivity and the reaction reagent is covered, like the method in Patent Document 5, with a hot-melt sealing compound, the sealing compound is melted by heat when the substrate and cover material were stuck together, posing a problem that the sealing compound flows out to a channel of the reaction chip to block the channel or the shape of the sealing compound when re-solidified becomes unstable, leading to incomplete sealing of the reaction reagent. Because of this problem, there is a possibility that contamination cannot be sufficiently prevented from occurring.

In these genetic tests, the amount of nucleic acid (DNA) contained in a sample is amplified by the polymerase chain reaction (PCR) for the test and an attempt is being made to make the test faster by reducing the time necessary for the PCR.

As a method of executing the PCR in a shorter time, an attempt is being made to execute the PCR with a smaller amount of sample and a reaction container and a reaction apparatus (temperature controlling unit) therefor are devised.

Most reaction containers are made of synthetic resin that does not inhibit a biological reaction and a reaction is caused by reducing a reaction volume to several tens microliter. In addition, in some instances, the reaction container is formed from aluminum.

In such reaction containers, a PCR reaction is allowed to occur without a minimum amount of sample being evaporated by a heating unit being brought into contact from above and below by a reaction apparatus described in Patent Document 6 or 7.

The reaction apparatus described in Patent Document 6 or 7 causes no big problem if the reaction container is formed from a single material. However, if a PCR reaction is allowed to occur by using a container constructed by separate materials having different thermal conductivities in an upper part and a lower part of the reaction container for the purpose of improving performance of the reaction container, the temperature distribution of the sample inside the reaction container becomes inhomogeneous due to a difference in thermal conductivity, posing a problem that the PCR reaction does not proceed smoothly.

Patent Document 1: Japanese Patent Application Laid-Open No. 2002-300894
Patent Document 2: Japanese Patent Application National Publication No. 2002-503336
Patent Document 3: Japanese Patent Application Laid-Open No. 9-257748
Patent Document 4: Japanese Patent No. 2955229
Patent Document 5: Japanese Patent Application Laid-Open No. 2007-090290
Patent Document 6: Japanese Patent No. 3661112
Patent Document 7: Japanese Patent No. 3686917

SUMMARY OF THE INVENTION

The present invention has been made to solve the above problems.

A first object of the present invention is to provide a reaction chip capable of easily feeding a liquid without surface modification of a reaction container and leaving bubbles behind and performing accurate detection and measurement of a desired reaction.

A second object of the present invention is to provide a reaction method capable of reliably preventing an occurrence of contamination and measuring accurate reaction data without lowering or devitalizing activity of a reaction reagent.

A third object of the present invention is to provide a temperature controlling unit for a gene treating apparatus and a gene treating apparatus capable of treating genes contained in a gene sample filled in a reaction container swiftly and appropriately even if the reaction container constructed from a plurality of materials having different thermal conductivities is used.

A thorough examination by the present inventors to attain the first object shows, as a result, that a conventional reaction container composed of a recess having a steep inner wall surface traps bubbles particularly in a space sandwiched between the inner wall surface present in a flow direction of a reagent solution and a bottom. Therefore, the present inventors conceive the constitution of the present invention by realizing that it becomes harder for bubbles to remain in a recess by making such an inner wall surface smaller and adopting a configuration that allows a reagent solution to flow smoothly near the recess.

A reaction chip in the present invention is a reaction chip having a plurality of reaction containers constituted by a pair of base materials to cause a reaction between a reagent and a reagent solution and a channel that mutually communicates the plurality of reaction containers to feed the reagent solution to the plurality of reaction containers, including forming a plurality of recesses constituting a part of the reaction container on at least one of one face of a first base material and one face of a second base material of the pair of base materials, forming a groove constituting a part of the channel at a position corresponding to between the recess and the recess on at least one of one face of the first base material and one face of the second base material, forming a notch showing a gradual increase in width and a gradual increase in depth from one face of the base material where the recess is formed toward an inner wall surface of the recess on an edge of at least one recess of the recesses in an extending direction of the groove, and forming the plurality of reaction containers and the channel by one face of the first base material and one face of the second base material being stuck together facing each other.

In the reaction chip of the present invention, an angle formed by one face of the base material where the recess is formed and the inner wall surface of the notch is smaller than the angle formed by one face of the base material where the recess is formed and the inner wall surface of the recess.

In the reaction chip of the present invention, the notch is formed on at least an inflow side of the reagent solution flowing through the groove on the edge of the recess in the extending direction of the groove.

In the reaction chip of the present invention, a configuration may be adopted in which the notch is formed on at least an outflow side of the reagent solution flowing through the groove on the edge of the recess in the extending direction of the groove so that the notch formed on the inflow side of the reagent solution and the notch formed on the outflow side of the reagent solution form a line symmetric shape.

In the reaction chip of the present invention, the recess has a columnar space having the inner wall surface at substantially right angles to one face of the base material where the recess is formed on at least an opening side, and the maximum depth on the edge of the notch is shallower than the depth of the columnar space.

An outer shape of the recess is circular in plane view and a plane shape of the notch is defined, when two tangents to a circle forming an outer edge of the recess are drawn from one point on one face of the base material where the recess is formed in the extending direction of the groove, by an area inside the two tangents.

In the reaction chip of the present invention, a center line in the extending direction of the groove of the notch is aligned with the center line of the groove on a same straight line.

To achieve the second object, a reaction method of the present invention is a reaction method using a reaction chip having a channel that mutually communicates a plurality of reaction containers constituted by a pair of base materials and the plurality of reaction containers, including the steps of arranging a reagent inside a recess by using, of the pair of base materials, the first base material having the recess constituting a part of the reaction container formed therein, sealing the reagent with a hot-melt sealing compound, producing the reaction chip having the reaction containers in which the reagent is arranged and the channel by sticking the second base material constituted by a material whose thermal conductivity is higher than that of the first base material and the first base material together, feeding a reagent solution into the reaction containers through the channel, and causing a reaction of the reagent and the reagent solution to proceed while heat being added from a side of the second base material after the reagent and the reagent solution being brought into contact by heating the reaction chip from the side of the second base material to melt the sealing compound.

In the reaction method of the present invention, the first base material and the second base material are stuck together through thermal welding of a sealant layer provided on at least one side of the first base material and the second base material by adding heat from the side of the second base material.

In the reaction method of the present invention, the recess corresponding to the recess in the first base material is also formed in the second base material to constitute the reaction container by both the recess of the first base material and the recess of the second base material.

In the reaction method of the present invention, a resin material is used as the first base material and a metallic material is used as the second base material.

In the reaction method of the present invention, the sealing compound is constituted by a material that is insoluble in neither the reaction reagent nor the reagent solution.

In the reaction method of the present invention, the reaction container is a reaction container for enzyme reaction.

To achieve the third object, a temperature controlling unit for gene treating apparatus of the present invention is a temperature controlling unit for gene treating apparatus that treats a gene inside a gene sample by heating/cooling the gene sample filled in a reaction container composed of a first member arranged in an upper part and a second member having a different thermal conductivity from that of the first member and arranged in a lower part, including a first temperature controlling unit arranged in such a way to allow contact with a top face of the reaction container, a second temperature controlling unit arranged in such a way to allow contact with an undersurface of the reaction container and also arranged in such a way to be able to sandwich the reaction container between the first temperature controlling unit and the second temperature controlling unit, a pair of metallic plates arranged on surfaces where the first temperature controlling unit or the second temperature controlling unit is in contact with the reaction container, a pair of heat conduction members arranged on surfaces of the pair of metallic plates facing the reaction container and also arranged in such a way to allow contact with the top face and the undersurface of the reaction container, a first heat dissipation unit provided in contact with the first temperature controlling unit, and a second heat dissipation unit provided in contact with the second temperature controlling unit.

According to a temperature controlling unit for gene treating apparatus of the present invention, heat of the first temperature controlling unit or the second temperature controlling unit is dissipated uniformly by a pair of metallic plates and transmitted efficiently to a reaction container by a pair of heat conduction members.

The temperature controlling unit for gene treating apparatus of the present invention further includes a control unit connected to the first temperature controlling unit and the second temperature controlling unit to control temperatures of the first temperature controlling unit and the second temperature controlling unit, wherein the control unit may exercise temperature control of the first temperature controlling unit and the second temperature controlling unit independently based on the thermal conductivities of the first member and the second member.

In this case, the temperature difference of a gene sample between the first member and the second member becomes smaller, so that the gene can be treated more suitably.

A gene treating apparatus of the present invention includes a temperature controlling unit for gene treating apparatus of the present invention.

According to a gene treating apparatus of the present invention, a gene can be treated quickly and suitably even if a reaction container composed of a first member and a second member is used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is an enlarged view of a recess of the resin base material.

FIG. 5 is a diagram showing another example of the recess.

FIG. 20 is an enlarged view of the recess of the reaction chip in Comparative Example 1.

1: Reaction chip, 2: Resin base material (first base material), 3: Metallic base material (second base material), 4: Reaction container, 5: Channel, 6: Recess (of a resin base material), 6a: Columnar space, 6b: Truncated cone shaped space, 11: Recess (of a metallic base material), 12: Groove, 15, 16: Notch, 21: Reaction chip, 22: Cover material (first base material), 23: Substrate (second base material), 24: Reaction container, 25: Channel, 26: Recess (of a cover material), 27: Recess (of a substrate), 28: Groove, 30: Reagent solution injecting hole, 31: Through hole, 41: Temperature controlling unit for gene amplifying apparatus, 42: Gene amplifying apparatus (gene treating apparatus), 43: Movable carriage, 44: Measuring unit, 45: Moving unit, 46: Rail, 47: Emission detection unit, 48: Measuring unit moving unit, 49: First unit, 50: Second unit, 51: Support arm, 52: First temperature controlling unit, 53: First heat sink (first heat dissipation unit), 54: Second temperature controlling unit, 55: Second heat sink (second heat dissipation unit), 56: First heat conduction layer, 58: Control unit, 59: Metallic plate, 60: Second heat conduction layer (heat conduction member), 61: Heat insulating material, 100: Reaction container, 101: First member, 102: Second member, 103: Well, 104: Reagent, 105: Channel, 106: Injecting hole, 107: Deaeration port, S: Reagent, W: Sealing compound, L: Reagent solution

DETAILED DESCRIPTION OF THE INVENTION

First Embodiment

An embodiment of the present invention will be described below with reference to FIGS. 1 to 7.

The present embodiment shows an example of a reaction chip for biochemical reaction analysis.

Figure 1:
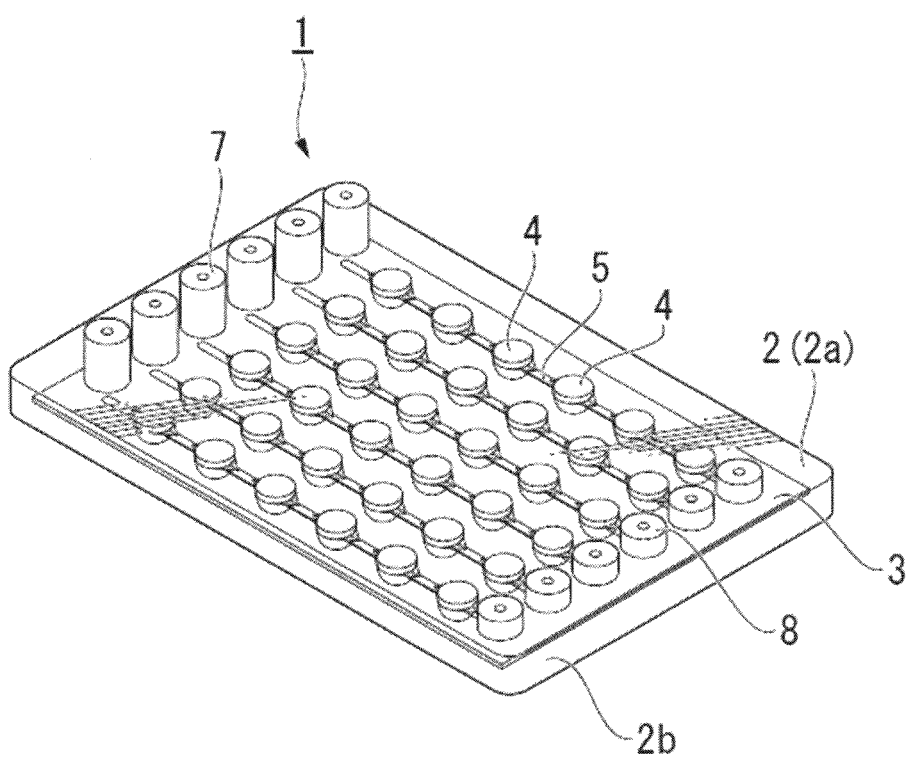
FIG. 1 is a perspective view of a reaction chip according to an embodiment of the present invention.
Figure 2:
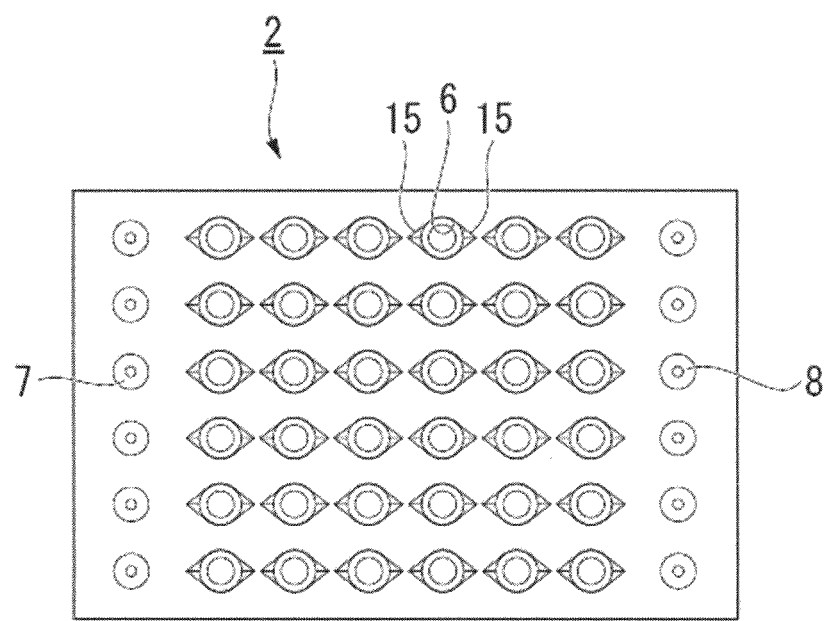
FIG. 2 is a plan view of a resin base material constituting the reaction chip.
Figure 3:
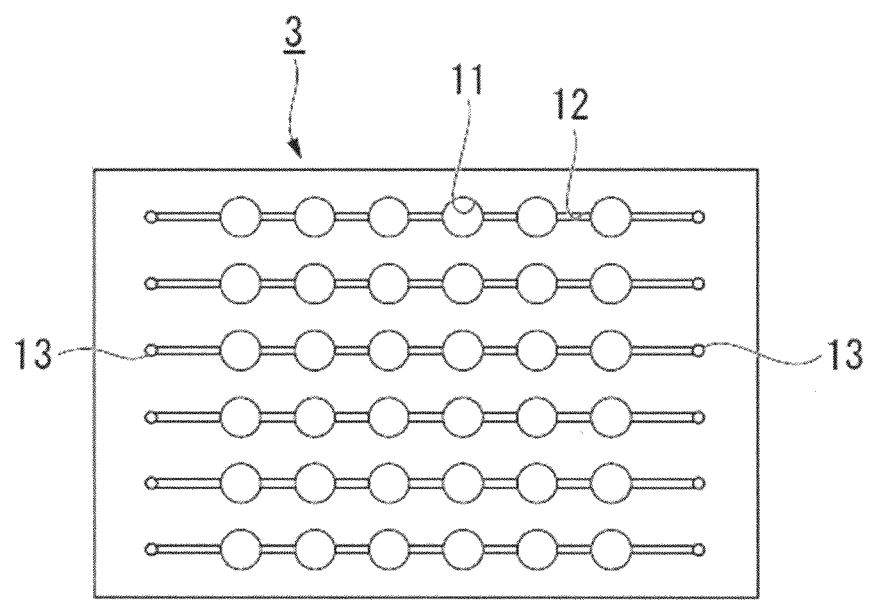
FIG. 3 is a plan view of a metallic base material constituting the reaction chip.
Figure 4A:
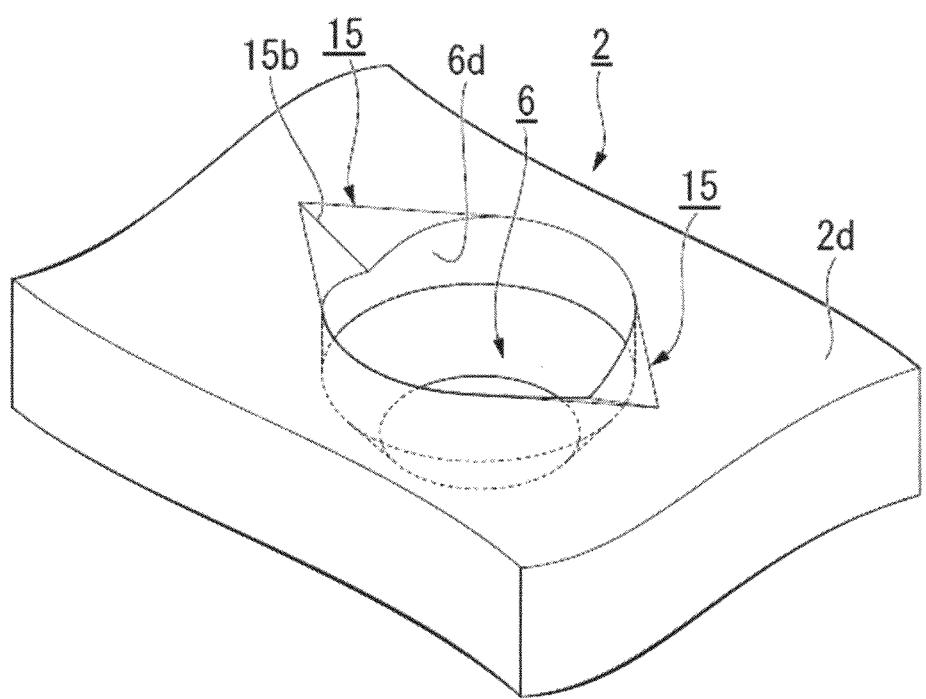
FIG. 4A is a perspective view thereof.
Figure 4B:
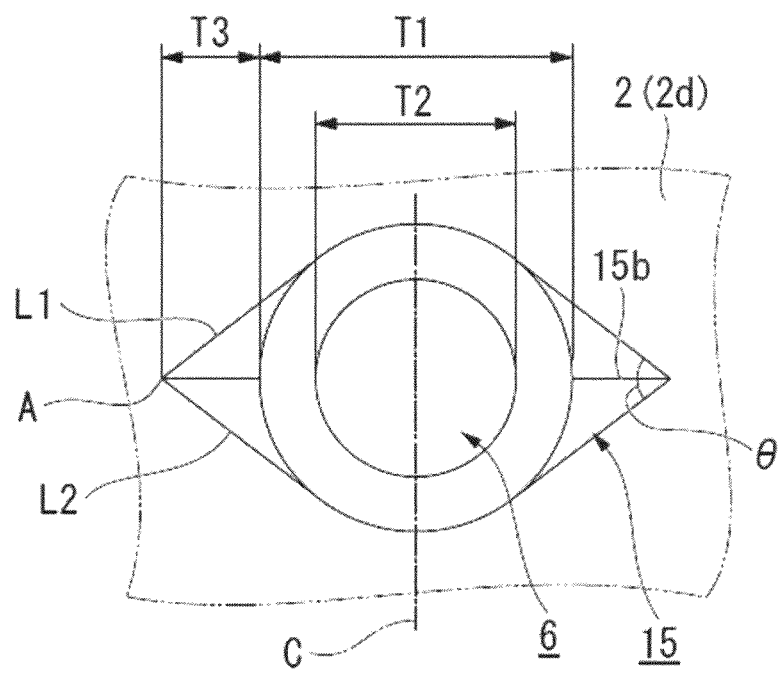
FIG. 4B is a plan view thereof.
Figure 4C:
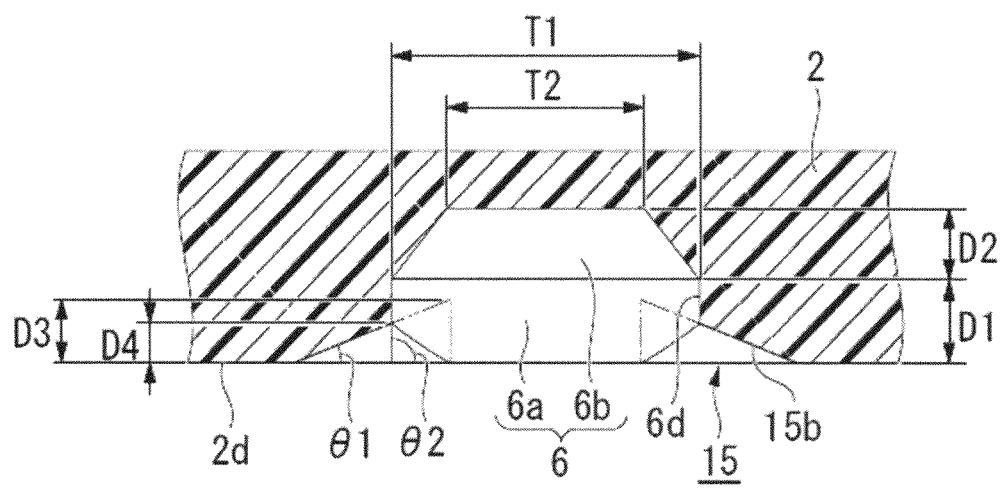
FIG. 4C is a side sectional view thereof.
Figure 5A:
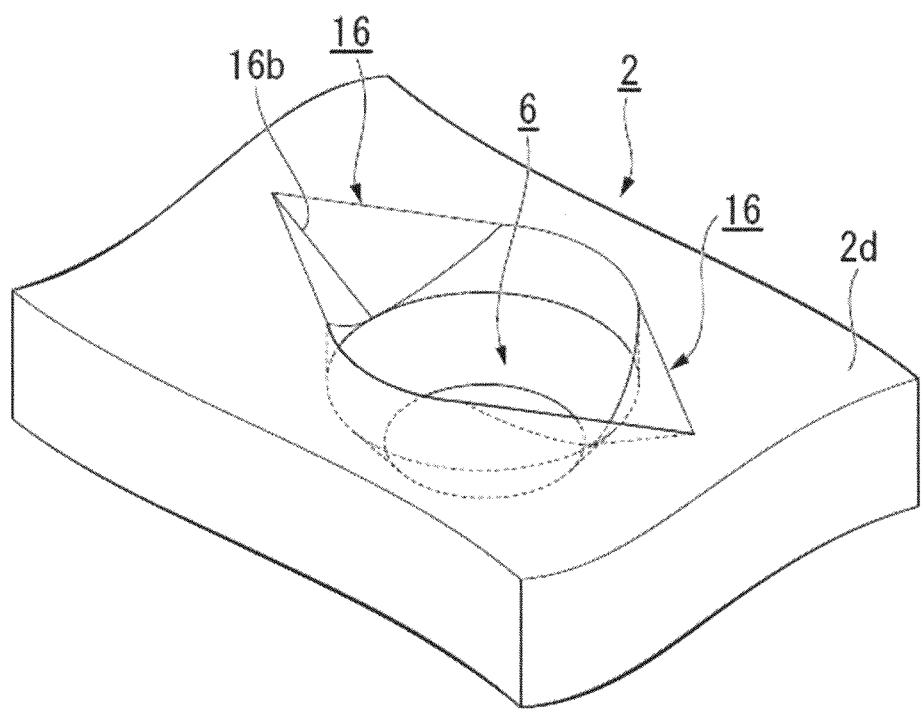
FIG. 5A is a perspective view thereof and FIG. 5B is a side sectional view thereof.
Figure 5B:
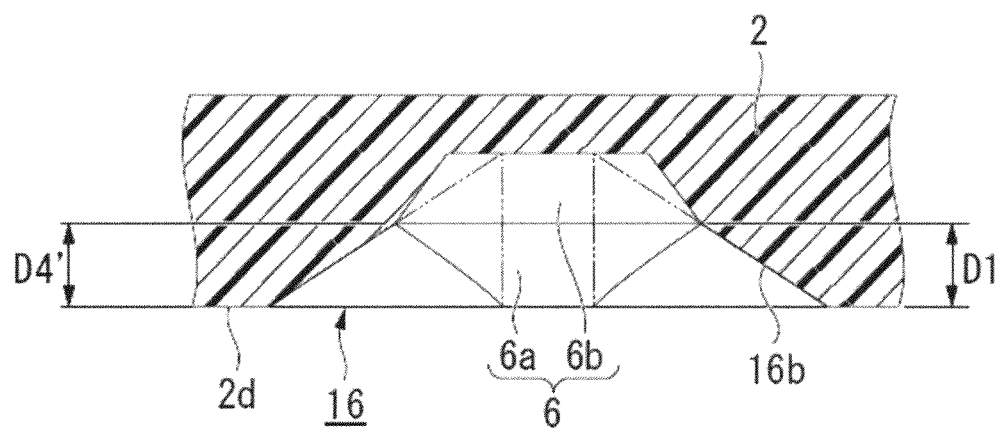
Figure 6A:
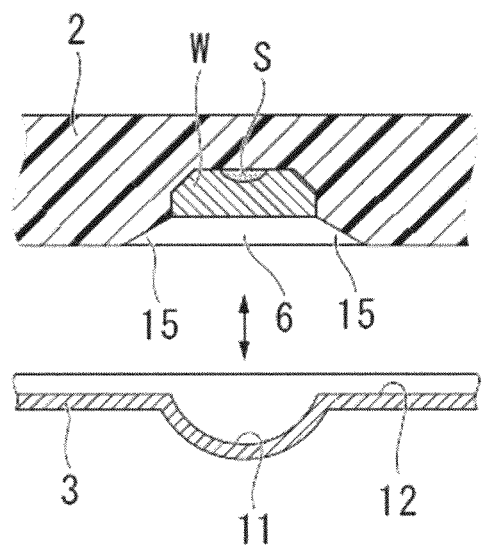
FIGS. 6A, 6B and 6C are process sectional views showing a reaction detection method using the reaction chip following procedures thereof.
Figure 6B:
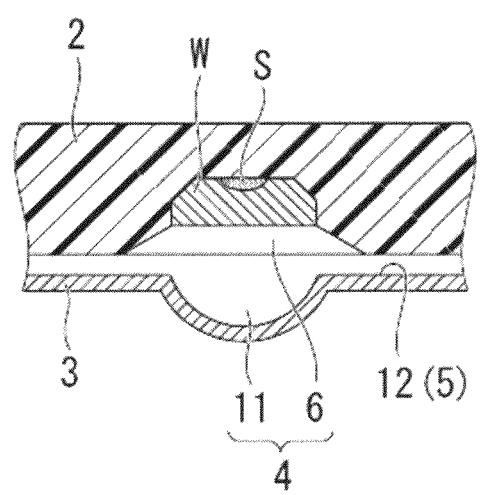
Figure 6C:
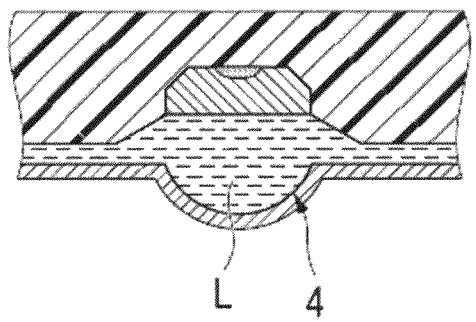

FIG. 1 is a perspective view of a reaction chip in the present embodiment. FIG. 2 is a plan view of a resin base material (first base material) constituting the reaction chip. FIG. 3 is a plan view of a metallic base material (second base material) constituting the reaction chip. FIGS. 4A to 4C are enlarged views of a recess of the resin base material and FIG. 4A is a perspective view thereof, FIG. 48 is a plan view thereof, and FIG. 4C is a side sectional view thereof. FIGS. 5A and 5B are diagrams showing another example of the recess and FIG. 5A is a perspective view thereof and FIG. 5B is a side sectional view thereof. FIGS. 6A to 6C are process sectional views showing a reaction detection method using the reaction chip following procedures thereof. FIG. 7 is a process sectional view when the reaction chip of another type is used.

For convenience of description, it is assumed below that the side of resin base material positioned on the upper side, when a fluorescent reaction is detected or measured, is the "upper side" and the side of metallic base material positioned on the lower side is the "lower side".

A reaction chip 1 in the present embodiment is a small chip that has, as shown in FIG. 1, a rectangular shape whose plane shape has about several tens mm both in length and width and a thickness of about several mm. The reaction chip 1 is constituted by a resin base material 2 (first base material) and a metallic base material 3 (second base material) arranged on the lower side of the resin base material 2. In the reaction chip 1 in the present embodiment, the resin base material 2 has recesses constituting reaction containers 4 formed therein and the metallic base material 3 has recesses constituting the reaction containers 4 and grooves constituting channels 5 formed therein.

A plate material of polypropylene superior in terms of light transmission, heat resistance, chemical resistance, molding workability, and strength may be used as the resin base material 2. In addition to this, a resin material such as polycarbonate, acryl(polymethyl methacrylate), polyethylene terephthalate, polyethylene, polyvinyl chloride, and polystyrene as materials having similar characteristics.

The thickness of the resin base material 2 is preferably such that the resin base material 2 should not easily be bent while being used. Moreover, the resin base material 2 may be formed by two types of resin or more being bonded. In such a case, various base materials in accordance with physical properties of the reaction reagent or sample can be produced by preparing base materials making the most of characteristics of each resin so that different base materials can be used for different purposes. For example, the material for the upper part and that for the lower part of the base material may be separated. Further, the material of base material is not limited to resin and quartz glass may also be used.

The resin base material 2 has, as shown in FIG. 2, a plurality (in the present embodiment 36 recesses, 6 rows×6 columns) of recesses 6 constituting a part of the reaction container 4 formed on the undersurface thereof. These recesses 6 do not mutually communicate and thus is isolated. The plane shape of the recess 6 is circular and the sectional shape thereof is, as shown in FIG. 4C, a columnar space 6a on the side closer to the undersurface of the resin base material 2 and a truncated cone shaped space 6b on the side farther from the undersurface. The shape of the recess 6 (together with the plane shape and sectional shape) can appropriately be designed such that the whole reagent can reliably be accommodated at the bottom of the recess 6 in accordance with the amount of reagents or reagent solutions necessary for a reaction. However, if, like the present embodiment, a configuration in which the recess has a truncated cone shaped space on the bottom side of a columnar space is adopted, a liquid settles down in a portion of the truncated cone shaped space with stability so that a reagent or a fixing agent can reliably be accommodated. Particularly, if the base material on the side on which a recess is formed is constituted by a material having light transmission, the flat bottom of the truncated cone shaped space is suitable for detection of a fluorescent reaction so that fluorescence can be detected accurately.

The recess 6 is formed by methods of cutting a resin plate constituting the resin base material 2, injection-molding a resin material constituting the base material or the like. In view of miniaturization of the reaction chip, the diameter of the recess 6 (the reaction container 4) is preferably about 0.01 mm or more and 10 mm or less. This makes feeding of a reagent solution described later relatively easier and can reduce the amount of a fixing reagent or reagent solution to a minimum. As described later, a reagent necessary for an incipient reaction of a sample containing DNA added when used is arranged in each of the recesses 6 of the resin base material 2. Alternatively, the reagent may be arranged only in a portion of the recesses 6 so that plural types of reactions can be caused in one reaction chip.

The configuration of the recess 6 will be described later.

As shown in FIGS. 1 and 2, a plurality (in the present embodiment, six) of reagent solution injecting holes 7 is provided at one end on the top face (the surface on the opposite side of the surface where the recesses 6 are formed) of the resin base material 2. The reagent solution injecting hole 7 is communicatively connected to a through hole (not shown) passing through a top plate part 2a of the resin base material 2 and is formed in a cylindrical shape protruding upward. Air discharge holes 8 are provided at the other end of the resin base material 2 on the opposite side of the side where the reagent solution injecting holes 7 are provided. The air discharge hole 8 has a cylindrical shape, has a through hole in the center, and has a filter (not shown) filled in the through hole. The filter has a function to smoothly pass a reagent solution by allowing air to pass through while the reagent solution flows. On the other hand, when the reagent solution that has flown through the channel reaches the air discharge hole 8, the filter has a function to prevent the reagent solution from flowing out by holding back the reagent solution. A frame part 2b that hangs down from the top plate part 2a is provided on the edge of the top plate part 2a of the resin base material 2, and the metallic base material 3 is arranged and fixed inside the frame part 2b.

An aluminum sheet, for example, can be used as the metallic base material 3 and a resin sealant layer (not shown) is formed on one side of the aluminum sheet. The resin sealant layer is made of polypropylene as a main material and is a bonding layer that can thermally be welded with the metallic base material 3 and the resin base material 2.

In addition to aluminum, copper, silver, nickel, brass, or gold may be used as the material of the metallic base material 3.

The metallic base material 3 has, as shown in FIG. 3, a plurality (in the present embodiment, 36) of recesses 11 constituting a part of the reaction container 4 formed on the top face of the metallic base material 3. These recesses 11 are formed at a position corresponding to the recesses 6 of the resin base material 2 when the metallic base material 3 and the resin base material 2 are aligned.

In contrast to the recess 6 of the resin base material 2, the sectional shape of the recess 11 has, as shown in FIG. 6, a substantially hemispheric shape. While the recesses 6 and 11 correspond one-to-one between the resin base material 2 and the metallic base material 3 in the present embodiment, one-to-one correspondence may not necessarily be realized or recesses of different sizes may be formed depending on purposes of use. In the present embodiment, the volume of the recess 6 and that of the recess 11 are substantially the same on the resin base material 2 side and the metallic base material 3 side.

Moreover, a groove 12 constituting a part of the channel 5 is formed between the recesses 11 on the top face of the metallic base material 3. The reaction chip 1 in the present embodiment has, as shown in FIGS. 1 and 3, six sets of the channel 5 and the six recesses 11 (reaction containers 4) are serially connected in one set of the channel 5. A slight recess 13 is formed at a position corresponding to each of the reagent solution injecting holes 7 and each of the air discharge holes 8, and the groove 12 is also formed between the recess 13 and the recess 11. Thus, a reagent solution injected from each of the reagent solution injecting holes 7 flows through the channel 5 and, after the six reaction containers 4 being filled successively, is held back by the filter of the air discharge holes 8.

The configuration of the recess 6 of the resin base material 2 will be described in detail below using FIGS. 4A to 4C. Incidentally, FIG. 4A alone is depicted by inverting vertically so that the shape of the recess 6 can be made easier to view.

The recess 6 has a circular shape with a diameter T1 as a plane shape, the columnar space 6a with the diameter T1 and a depth D1 as a sectional shape on the side closer to the undersurface of the resin base material 2, and the truncated cone shaped space 6b with a diameter T2 of the circle at the bottom and a depth D2 as a sectional shape on the side farther from the undersurface (bottom side of the recess). A notch 15 showing a gradual increase in width and a gradual increase in depth from an undersurface 2d of the resin base material 2 toward an inner wall surface 6d of the recess 6 is formed on edges of both an inflow side and an outflow side of a reagent of the recesses 6 along an extending direction of the groove 12 (the channel 5). The notch 15 on the inflow side and that on the outflow side of a reagent have the same shape and are arranged, as shown in FIG. 4B, symmetrically with respect to a center line C extending in a direction perpendicular to the extending direction of the groove 12. The notch 15 on the inflow side and that on the outflow side of a reagent may have different shapes and may not necessarily be symmetric with respect to the center line C.

As shown in FIG. 4A, the notch 15 has a shape cut out like a triangular pyramid shape from the undersurface 2d of the resin base material 2 toward the inner wall surface 6d of the recess 6 in the extending direction of the groove 12. Therefore, the bottom of the notch 15 forms an acute valley line 15b. In the columnar space 6a of the recess 6, the inner wall surface 6d rises steeply at substantially right angles to the undersurface 2d of the resin base material 2 and, as shown in FIG. 4C, an angle θ1 formed by the undersurface 2d of the resin base material 2 and the valley line 15b of the notch 15 becomes sufficiently smaller than an angle θ2 (θ2≈90°) formed by the undersurface 2d of the resin base material 2 and the inner wall surface 6d of the recess 6 due to formation of the notch 15. The bottom of the notch 15 need not necessarily be an acute valley line and may be, for example, a gently curved surface.

The plane shape of the notch 15 is defined, when two tangents L1 and L2 to a circle forming an outer edge of the recess 6 are drawn from any point A on the undersurface 2d of the resin base material 2 in the extending direction of the groove 12, as shown in FIG. 4B, by an internal area enclosed by the two tangents L1 and L2 and the circle. If the angle formed with the two tangents L1 and L2 is θ, θ is preferably 5° or more. This is because θ of 5° or less makes processing harder and also an effect of bubble removal is hardly achieved. A distance T3 from the point A to an intersection of the valley line 15b of the notch 15 and the circle can be appropriately decided in accordance with an interval between the adjacent recesses 6 of the resin base material 2. The recess 6 is designed such that the center line (the valley line 15b) along the extending direction of the groove 12 of the notch 15 is aligned with the center line of the groove 12 of the metallic base material 3 on the same straight line. With the above plane shape, the plane shape of each of the recesses 6 in the present embodiment has a shape that has sufficiently small flow resistance so that a reagent solution flows extremely smoothly.

On the other hand, the sectional shape when the notch 15 is cut along the center line extending in the extending direction of the groove 12 of the notch 15 is as shown in FIG. 4C. Lines represented as solid lines are what visually appears of the notch 15 and those represented as chain double-dashed lines are a (virtual) triangle for design when the recess 6 is designed so that the notch 15 is cut out in a triangular shape as the sectional shape. The virtual depth at a vertex positioned inside the columnar space 6a of the triangle is set as D3. Consequently, the point where the valley line 15b of the notch 15 and the inner wall surface 6d of the recess 6 (the columnar space 6a) intersect is a point where the distance of the intersection point from the undersurface 2d of the resin base material 2 becomes a maximum depth D4 of the notch 15.

Examples of dimensions in the present embodiment are: the diameter T1 of the recess (columnar space) is 3 mm, the diameter T2 of the truncated cone shaped space is 2 mm, the distance T3 from the point A to an intersection of the valley line 15b of the notch 15 and the circle is 1 mm, the depth D1 of the columnar space 6a is 0.8 mm, the depth D2 of the truncated cone shaped space 6b is 0.7 mm, and the virtual depth D3 at a vertex positioned inside the columnar space 6a of the virtual triangle is 0.6 mm. These dimensions are only examples and the design can be changed when appropriately.

In the example shown in FIG. 4C, the depth D4 to be the maximum depth of the notch 15 is shallower than the depth D1 of the columnar space 6a of the recess 6. Thus, even if the notch 15 is formed on the edge of the columnar space 6a, the vertical inner wall surface 6d in the columnar space 6a of the recess 6 remains at the position of the valley line 15b of the notch 15. Therefore, in this example, a volume capable of accommodating reagents or wax described later can be ensured and also reagents or wax can reliably be accommodated inside the columnar space 6a and the truncated cone shaped space 6b so that the top face of the wax is positioned in a part of the columnar space 6a in which the vertical inner wall surface 6d remains.

Alternatively, as shown in FIGS. 5A and 5B, a design in which a dimension D4' to be the maximum depth of a notch 16 is made equal to the depth D1 of the columnar space 6a of the recess 6 may be adopted. In this case, the size of the notch 16 becomes substantially larger than the configuration shown in FIG. 4B and no vertical inner wall surface in the columnar space 6a of the recess 6 remains at the position of a valley line 16b of the notch 16. In this example, while the volume of the space to accommodate reagents or wax is slightly reduced when compared with the configuration shown in FIG. 4B, reagents are made easier to flow, so that bubbles can be prevented from remaining.

A manufacturing method of a reaction chip in the present embodiment will be described below using FIGS. 6 and 7.

As shown in FIG. 6A, after a resin sealant layer is formed on one side of an aluminum sheet to produce a base material sheet, the metallic base material 3 including a plurality of recesses 11 and a plurality of grooves 12 is produced by a method of drawing on the base material sheet or the like. On the other hand, the resin base material 2 having a plurality of recesses 6 is formed by a method of injection molding or the like. Then, the notch 15 is formed on the edge of the recess 6 by a method of cutting or the like. Any cutting method can be selected. The resin base material 2 including the plurality of recesses 6 having the notch 15 from the start may be produced by the method of injection molding or the like.

Next, the opening of the recess 6 is directed upward and a reagent S is put into the plurality of recesses 6 of the resin base material 2 before being fixed. Further, the reagent S is covered with wax W before being solidified. The wax (fixing material) herein is a material that covers the reagent arranged inside the recess 6 and remains in a solid state until a reaction between a reagent and a reagent solution begins. The wax may be a single material or made up of a plurality of materials (for example, a mixture). In embodiments of the present embodiment, hot-melt wax is used, but wax that is melted by a factor other than heat or breaks so that a reagent and a reagent solution mix may be adopted. Any kind of wax that does not prevent a reaction between a reagent and a reagent solution but melts at a necessary temperature may be selected.

The reagent used in the present invention may be in a solid state or a liquid state.

Next, as shown in FIG. 6B, the resin base material 2 to which the reagent S is fixed is placed on top of the metallic base material 3 such that surfaces on which the mutual recesses 6 and 11 are formed face each other and then heat is added. The resin sealant layer on the surface of the metallic base material 3 melts and the resin base material 2 and the metallic base material 3 are welded. With the above processes, a reaction chip including a plurality of reaction containers 4 and a plurality of channels 5 is completed.

The method of thermal welding can be appropriately selected from methods such as the heat sealer, laser welding, and ultrasonic welding. Alternatively, instead of welding, the resin base material 2 and the metallic base material 3 may be stuck together. In such a case, an adhesive used for pasting can appropriately be selected from any adhesive on the market that does not inhibit the target reaction. Alternatively, a method of mechanical crimp by a roller or the like with involvement of an adhesive material between the resin base material 2 and the metallic base material 3 may be adopted.

Next, as shown in FIG. 6C, a reagent solution L is fed into each of the reaction containers 4 of the completed reaction chip. After the reagent solution L being fed, the channel 5 is blocked by plastically deforming a part of the groove 12 of the metallic base material 3 to isolate each of the reaction containers 4. By isolating each of the reaction containers 4, mixing of unnecessary reagents between the adjacent reaction containers 4 can be prevented. As a means for plastic deformation of the groove 12 of the metallic base material 3, an external force may mechanically be applied to a part of the groove 12 from outside by using a device, or an external force may be applied by hand. Then, when the temperature of the reaction chip 1 is controlled to a predetermined temperature (the melting point of the wax W or higher), the solidified wax W is melted and the reagent S and the reagent solution L are mixed inside the reaction container 4, initiating a reaction. In the present embodiment, the resin base material 2 made of polypropylene has greater transparency, so that fluorescence during reaction can be detected from outside on the side of the resin base material 2.

Figure 7A:
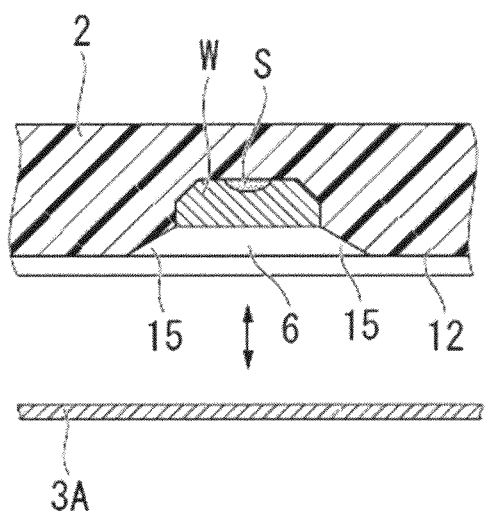
FIGS. 7A, 7B and 7C are process sectional views when the reaction chip of another type is used.
Figure 7B:
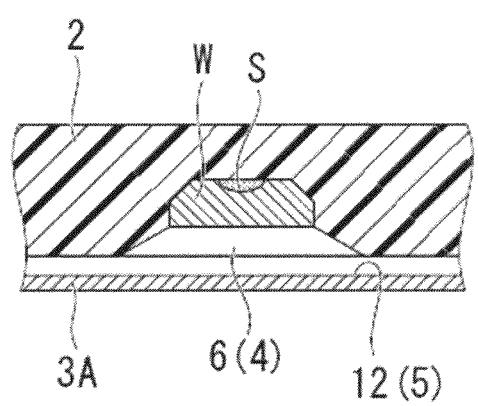
Figure 7C:
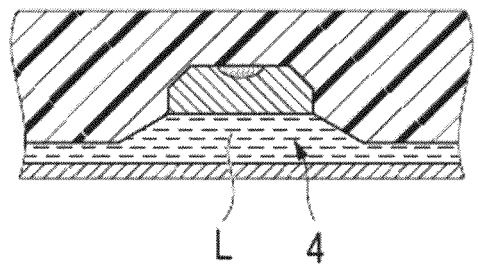

In the foregoing, the manufacturing method of a reaction chip in the present embodiment has been described by using an example of a reaction chip having the recess 11 and the groove 12 formed on the side of the metallic base material 3, but a configuration in which the recesses and grooves are all formed on the side of the resin base material and a flat plate material or a film 3A (a material other than metal is also allowed) is used on the side of the metallic base material to cover the recesses of the resin base material with the flat plate material or the film 3A may be adopted. An example thereof is shown in FIGS. 7A to 7C. This example is different from the above example only in which base material to form the recesses and grooves and the basic manufacturing processes are the same and thus, the same reference numerals are attached to components in FIGS. 7A to 7C that are common to those in FIGS. 6A to 6C and a description thereof is omitted.

The reaction chip 1 in the present embodiment has the notch 15 formed on the edges on the inflow side and outflow side of the reagent L of the recesses 6 formed on the resin base material 2 and thus, the reagent solution L flows smoothly near the recess 6 so that the inflow of the reagent solution L from the channel 5 into the reaction container 4 and the outflow of the reagent solution L from the reaction container 4 to the channel 5 become smooth. Thus, even if the reagent solution L containing bubbles flows in, bubbles pass through the reaction container 4, so that the frequency of bubbles remaining the recess 6 can significantly be decreased. As a result, the desired reaction can accurately be detected or measured by using the reaction chip 1 in the present embodiment. Moreover, there is no need of hydrophobic/hydrophilic treatment and surface treatment such as corona treatment and plasma treatment because bubbles can be removed from inside the recess 6 only by forming the notch 15 on the edge of the recess 6.

The technical scope of the present invention is not limited to the above embodiment and various modifications can be made without deviating from the spirit of the present invention. For example, while grooves constituting a channel are formed only in the metallic base material in the above embodiment, grooves may also be formed in the resin base material in accordance with the volume of a reagent solution so that the channel is constituted by both the metallic base material and resin base material. Further, an example in which the reaction contains have all the same size is described in the above embodiment, but instead thereof, a plurality of reaction containers having different sizes may be included. In this case, the shape or dimensions of the notch may be optimized by adjusting to the size of each reaction container. Moreover, concrete configurations such as the shape, number, and arrangement of the reaction containers and channel, materials and dimensions of each base material, various methods used in each manufacturing process exemplified in the above embodiment are only examples and may be changed when appropriate.

Second Embodiment

An embodiment of the present invention will be described below with reference to FIGS. 8 to 11.

Figure 8:
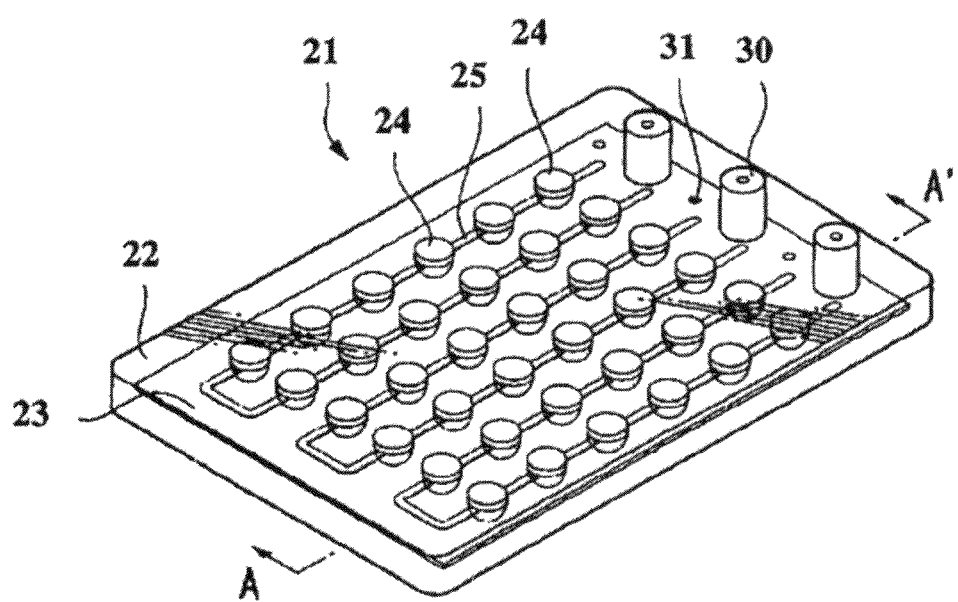
FIG. 8 is a perspective view of a reaction chip in an embodiment of the present invention.
Figure 9A:
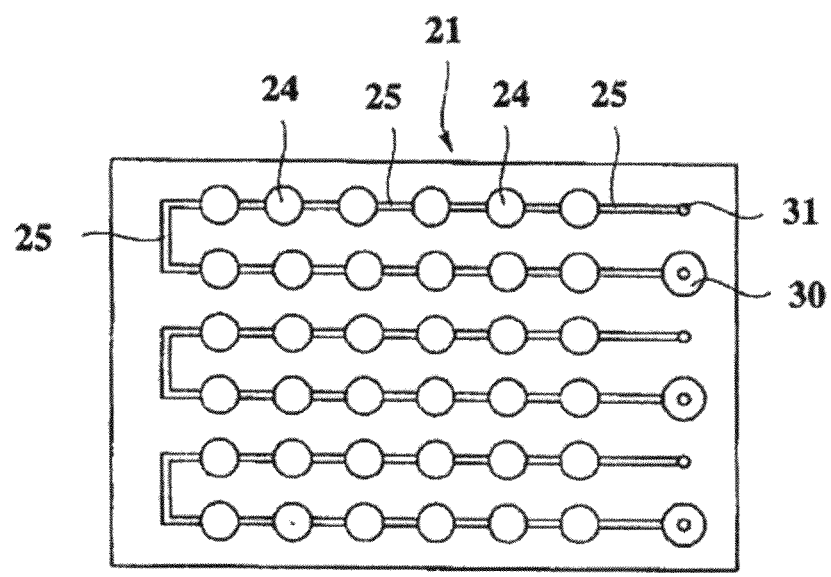
FIG. 9A is a plan view of the reaction chip and FIG. 9B is a sectional view along a line A-A' in FIG. 8.
Figure 9B:
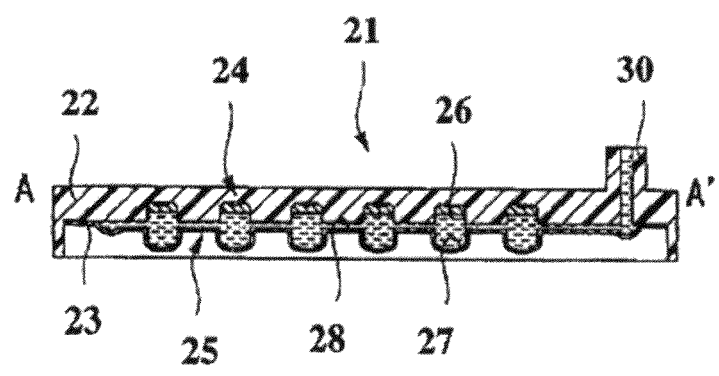

FIG. 8 is a perspective view of a reaction chip in the present embodiment. FIG. 9A is a plan view of the reaction chip and FIG. 9B is a sectional view along a line A-A' in FIG. 8. FIG. 10 is a process sectional view showing a reaction method using the reaction chip following procedures thereof. FIG. 11 is a sectional view showing another example of the reaction chip.

For convenience of description, it is assumed below that side of the resin base material positioned on the upper side, when a fluorescent reaction is detected or measured, is the "upper side" and the side of metallic base material positioned on the lower side is the "lower side".

A reaction chip 21 in the present embodiment is a small chip that has, as shown in FIG. 8, a rectangular shape and a thickness of about several mm. The reaction chip 21 is constituted by a cover material 22 (first base material) and a substrate 23 (second base material) embedded on the side of the undersurface of the cover material 22. The reaction chip 21 in the present embodiment has, as shown in FIG. 9B, recesses 26 constituting reaction containers 24 formed in the cover material 22 and grooves 28 constituting recesses 27 and channels 25 formed in the substrate 23. The reaction chip 21 in the present embodiment includes three sets of the channels 25 having the 12 reaction containers 24.

(Cover Material)

The cover material 22 presents a rectangular shape as a whole and is formed to such a thickness that the cover material 22 is not easily bent while being used. The cover material 22 is constituted by a resin material such as PP (polypropylene), PC (polycarbonate), acryl resin (polymethylmethacrylate), PET, (polyethylene terephthalate), PE (polyethylene), PV (polyvinyl chloride), and PS (polystyrene). The cover material 22 produced by using such a synthetic resin is preferable due to superiority in heat resistance, chemical resistance, and molding workability. Further the cover material 22 produced by two types of resin or more being bonded may be used. In such a case, various kinds of the cover materials 22 in accordance with properties of the reaction reagent or reagent solution can be produced by preparing the cover material 22 making the most of characteristics of each resin, so that the different cover materials 22 can be used for different purposes. For example, the material for the upper part and that for the lower part of the cover material 22 may be separated. Incidentally, in addition to resin materials, quartz glass or the like may be used as the material of the cover material 22.

The cover material 22 has, as shown in FIGS. 9A and 9B, a plurality (in the present embodiment, 36) of recesses 26 in which a reagent is arranged and a reagent solution injecting hole 30 communicatively connected to the reaction container 24 and the channel 25 to feed a reagent solution provided therein. In one set of the channel 25, a minute through hole 31 is provided at the end on the opposite side of the reagent solution injecting hole 30 and a high-density filter (not shown) is filled inside the through hole 31. Accordingly, a fed reagent solution can be prevented from overflowing from an outlet. Alternatively, a similar reagent solution injecting hole may be provided at the end on the opposite side of the reagent solution injecting hole 30 so that a reagent solution can be injected through whichever of the reagent solution injecting holes of the channel 25. The inner side of the reagent solution injecting hole 30 is preferably tapered so that the tip of a dispensing chip for general PIPETMAN fits in halfway through the injecting hole. Accordingly, feeding of a reagent solution is made easier and the mixing of bubbles can be prevented. Moreover, contamination of the apparatus due to scattering of a reagent solution during reaction can be prevented by providing a lid covering the reagent solution injecting hole 30 and a structure on the outlet side.
(Substrate)

The substrate 23 presents a rectangular shape as a whole. The substrate 23 is constituted by materials containing metal such as gold, silver, copper, aluminum, zinc, tin, platinum, nickel, brass, or alloys of at least two of these metals. Producing the substrate 23 using materials containing such metals makes the thermal conductivity to a reaction liquid in the reaction container 24 higher so that the reaction can preferably be caused to occur efficiently in a short time. Moreover, a sealant layer (not shown) is provided in an upper part of the metallic layer of the substrate 23 to stick the cover material 22 and the substrate 23 together by thermal welding. According to this configuration, a metal that inhibits a reaction can also be used because the metal constituting the substrate 23 does not come directly into contact with a reaction liquid.

The substrate 23 has a plurality (in the present embodiment, 36) of recesses 27 formed at positions corresponding to the recesses 26 of the cover material 22 and the grooves 28 to feed a reagent solution to allow communicative connection between the adjacent recesses 27. The diameter of the recess 27 is preferably almost the same as that of the recess 26 of the cover material 22. Accordingly, a reaction reagent solution can be fed equally to the recesses 26 and the recesses 27 and also the mixing of bubbles can be prevented. The width and depth of the channel 25 are preferably 0.5 mm or more and 5 mm or less. If the width and depth are within these dimensions, channel blockage caused by extrusion of the sealant layer into the channel when the cover material 22 and the substrate 23 are stuck together can be prevented and also the mixing of bubbles can be prevented.
(Reaction Container)

Figure 10A:
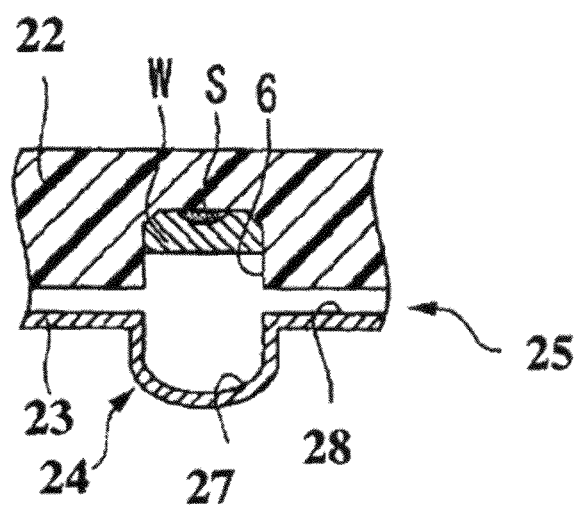
FIGS. 10A, 10B and 10C are process sectional views showing a reaction method using the reaction chip following procedures thereof.
Figure 11:
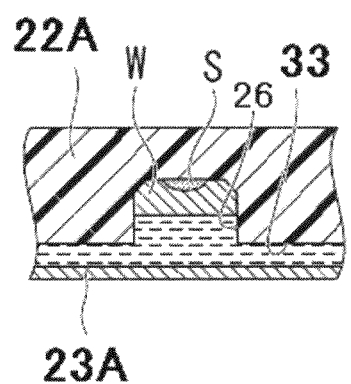
FIG. 11 is a sectional view showing another example of the reaction chip.

As shown in FIG. 10A, a lower area facing the substrate 23 of the recess 26 on the cover material 22 side is a columnar space and an upper (bottom side) area is a truncated cone shaped space. As shown in this case, the bottom of the recess 26 is preferably flat. Accordingly, when a reaction result is obtained by fluorescence detection through the transparent cover material 22, diffusion of light is reduced when compared with a case where the bottom is not flat and fluorescence can efficiently be detected. The diameter of the recess 26 is preferably 0.5 mm or more and 10 mm or less. Accordingly, feeding of a reagent solution to the recess 26 is made easier and the mixing of bubbles can be prevented.

The recess 27 on the substrate 23 side has, as shown in FIG. 10A, a hemispheric shape. If the recess 27 in a lower part of the reaction container 24 is formed in a hemispheric shape, convection is efficiently caused inside the reaction container 24 when heat is added for a reaction after a reagent solution being filled so that the reaction can be made to proceed more smoothly. If the shape of the reaction container 24 is formed into a shape similar to that of a tube made of PP generally used for PCR, adhesion property to a heat block that adds heat for a reaction is increased, so that heat can be transmitted efficiently to a reaction liquid, allowing the reaction to proceed in a short time.

The recess 26 is forted by a method of cutting the cover material 22 made of resin material or a method of injection-molding a resin material inside a die. If the cover material 22 is constituted by a hard resin material such as PC (polycarbonate), the recess 26 can be formed using the cutting method. If the cover material 22 is constituted by a soft resin material such as PP (polypropylene), the recess 26 is preferably formed using the molding method. The recess 26 can also be formed from PC using the molding method.

On the other hand, the recess 27 and the groove 28 are formed by a method of performing drawing using a die on the substrate 23 in which a metallic layer and a sealant layer are stuck together by an adhesive or the like.
(Sealing Compound)

As shown in FIG. 10A, a fixing reagent S such as a nucleic acid probe is arranged inside the recess 26 of the cover material 22. The fixing reagent S is covered with a hot-melt sealing compound W arranged inside the recess 26. The hot-melt sealing compound W is a sealing compound that is in a solid state at ordinary temperature and melts near a starting temperature of a reaction of the fixing reagent and a reagent solution (hereinafter, referred to as a "main reaction"). The melting point thereof is preferably near 35 to 90° so that sealing compound W melts at least near 80 to 90°. It is preferable to adopt a sealing compound whose specific gravity is smaller than that of the fixing reagent and also that of the reagent solution as the sealing compound W. However, the premise is that the main reaction is not inhibited. As a concrete sealing compound, AmpliWax (registered trademark) PCR Gem 100 manufactured by Applied Biosystems can be adopted. This is a product invented as a replacement of mineral oil so that evaporation of a reaction reagent solution is prevented by forming a layer after melting when a PCR amplification reaction occurs. This product is in a solid state at ordinary temperature and melts at 55 to 58°. The fixing reagent S covered with the sealing compound W may be in a liquid state or a solid state. If the fixing reagent S is in a liquid state whose specific gravity is larger than that of the reagent solution, or the melted sealing compound W has a specific gravity larger than that of the fixing reagent S and that of the reagent solution, it is easier and more advantageous to mix the fixing reagent S and the reagent solution.

To arrange the sealing compound W inside the recess 26, a method of injecting a proper amount of the solid sealing compound W into the recess 26 in which the fixing reagent S is pre-arranged and heating the sealing compound W can be used.

Accordingly, the melted sealing compound W spreads at the bottom of the recess 26 while wetting the bottom and, if the sealing compound W is cooled thereafter, the sealing compound W can be arranged inside the recess 26 while the fixing reagent S being covered therewith. Alternatively, a method of dispensing the pre-melted sealing compound W into the recess 26 in which the fixing reagent S is pre-arranged using PIPETMAN may be used. This method is more advantageous because the amount of the sealing compound W can be defined more accurately.

Further, it is preferable to perform a centrifugal operation before cooling the melted sealing compound W while wetting and spreading at the bottom of the recess 26. Accordingly, the sealing compound W can hide the fixing reagent S more reliably. Moreover, the sealing compound W on the wall surface of the recess 26 moves to the bottom of the recess 26 and thus, when the cover material 22 and the substrate 23 are stuck together by thermal welding, the outflow of the sealing compound W to the channel 25 due to re-melting can be prevented.

In this manner, the sealing compound W is arranged inside the recess 26 before the substrate 23 being stuck together.
(Reaction Method)

Next, the reaction method using the above reaction chip will be described using FIGS. 8 to 10.

Figure 10B:
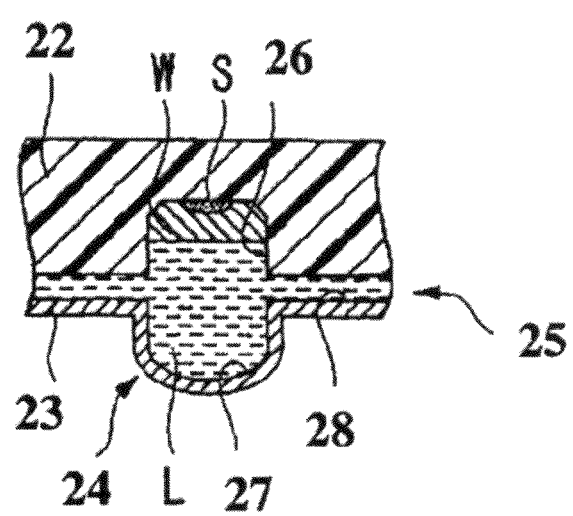

First, the reagent solution L is injected through the reagent solution injecting hole 30 shown in FIGS. 8 and 9. In this manner, as shown in FIG. 10B, the reagent solution L is passed from the reagent solution injecting hole 30 into the channel 25. Then, the reagent solution L passes through the channel 25 before being fed into a plurality of the reaction containers 24 one by one. The feeding of the reagent solution L occurs at ordinary temperature or a lower temperature below the ordinary temperature at which the reagent solution L can be fed.

Here, as shown in FIG. 10B, the solid sealing compound W in a state covering the fixing reagent S is arranged inside the recess 26 on the cover material 22 side. Thus, the reagent solution L fed to the reaction container 24 is arranged on the surface of the sealing compound W without coming into contact with the fixing reagent S.

Thus, in the reaction chip 21 in the present embodiment, the reagent solution L is fed below the sealing compound W covering the fixing reagent S, so that the fixing reagent S will not flow out to the adjacent reaction containers 24. Therefore, contamination can be prevented from occurring.

After the reagent solution L being fed into the reaction container 24, the channel 25 is blocked by plastically deforming a part of the groove 28 between the adjacent recesses 27 of the substrate 23 to isolate each of the reaction containers 24. By isolating each of the reaction containers 24, mixing of unnecessary reagents between the adjacent reaction containers 24 can be prevented.

As means for plastic deformation of the groove 28 of the substrate 23, an external force may mechanically be applied to a part of the groove 28 from outside by using a device or an external force may be applied by hand.

Figure 10C:
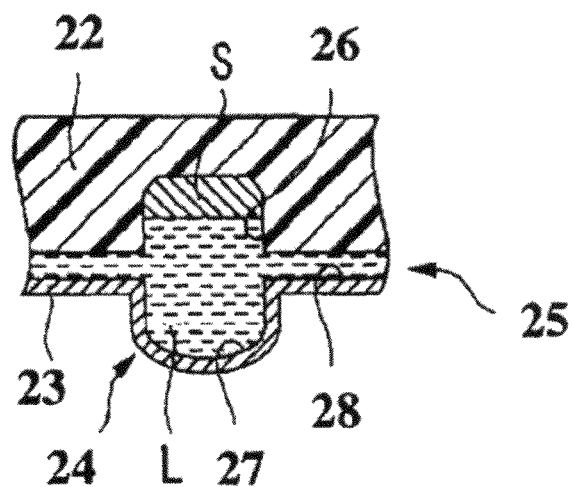

Next, as shown in FIG. 10C, the reaction container 24 is heated to melt the sealing compound W. At this point, heat is added not from the cover material 22 side where the fixing reagent S is arranged, but from the substrate 23 side. If the specific gravity of the sealing compound W is smaller than that of the fixing reagent S and also that of the reagent solution L, the sealing compound W changes places with the fixing reagent S vertically when melted and the fixing reagent S comes into contact with the reagent solution L. If the specific gravity of the sealing compound W is larger than that of the fixing reagent S and also that of the reagent solution L, the sealing compound W changes places with the reagent solution L vertically when melted and the reagent solution L comes into contact with the fixing reagent S. If the reaction initiation temperature of the main reaction is equal to the melting point of the sealing compound W or higher than the melting point of the sealing compound W, the fixing reagent S and the reagent solution L come into contact while being heated to the reaction initiation temperature and the main reaction is initiated when the reaction initiation temperature is reached.

If the reaction initiation temperature of the main reaction is lower than the melting point of the sealing compound W, the reaction container 24 is further heated to bring the fixing reagent S into contact with the reagent solution L and then, the temperature is lowered to the reaction initiation temperature to initiate the main reaction. In the present embodiment, heat is added during reaction from the substrate 23 side.

According to the reaction method in the present embodiment, the reaction chip 21 is constituted by the cover material 22 made of resin having a relatively low thermal conductivity and the substrate 23 made of metal having a relatively high thermal conductivity and the fixing reagent S is arranged inside the recess 26 of the cover material 22. When a reaction is caused, heat is added from the substrate 23 side with a high thermal conductivity and the sealing compound W is melted to bring the fixing reagent S and the reagent solution L into contact before causing the reaction to proceed. Therefore, when the reagent solution L is fed, the reagent S is covered with the sealing compound W so that contamination can be prevented from occurring. While thermal efficiency for the whole reaction container 24 can be made better by adding heat from the substrate 23 side, the reagent S is arranged on the cover material 22 side with a low thermal conductivity and thus, it is hard for heat during chip manufacturing to conduct to the reagent S so that activity of the reagent S is neither lowered nor devitalized. Accordingly, accurate reaction data can be measured.

The technical scope of the present invention is not limited to the above embodiment and various modifications can be made without deviating from the spirit of the present invention. For example, the recess 27 constituting the reaction container 24 and the groove 28 constituting the channel 25 are formed on the substrate 23 side in the above embodiment, but as shown in FIG. 11, a groove 33 may be formed on a cover material 22A side so that a flat plate is used as a substrate 23A in accordance with the volume necessary for the reaction container. Alternatively, the grooves 28 constituting the channel 25 are formed only in the substrate 23 in the above embodiment, grooves may also be formed on the cover material 22 side in accordance with the volume of the reagent solution L so that the channel may be constituted by both the cover material 22 and the substrate 23. Moreover, concrete configurations such as the shape, number, and arrangement of the reaction containers and channels, materials and dimensions of each base material, various methods used in each manufacturing process exemplified in the above embodiment are only examples and may be changed when appropriate.

Third Embodiment

A temperature controlling unit for a gene treating apparatus (hereinafter, referred to as a "temperature controlling unit") according to an embodiment of the present invention will be described below with reference to FIGS. 12 to 19.

Figure 12:
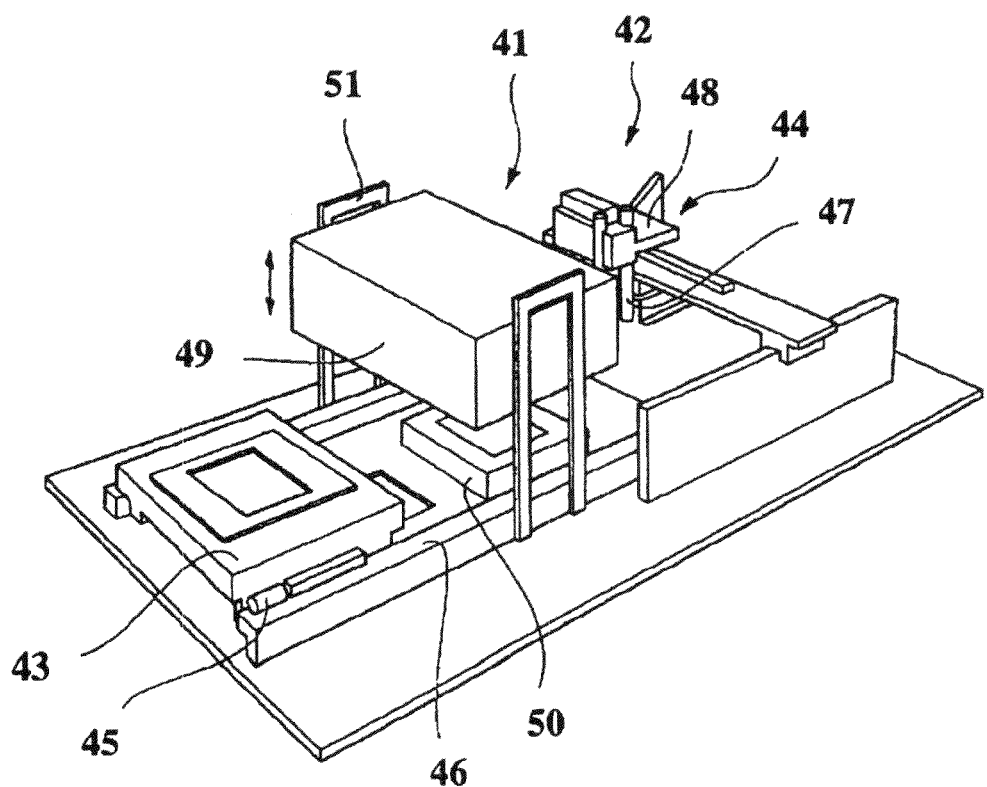
FIG. 12 is a perspective view showing the configuration of a gene amplifying apparatus including a temperature controlling unit for gene amplifying apparatus according to an embodiment of the present invention.

FIG. 12 is a perspective view showing principal parts of a gene amplifying apparatus (gene treating apparatus) 42 including a temperature controlling unit 41 in the present embodiment. The gene amplifying apparatus 42 includes a movable carriage 43 on which a reaction container is placed, the temperature controlling unit 41 that heats or cools the reaction container, and a measuring unit 44 that measures a reaction in the reaction container.

The movable carriage 43 is formed in a frame shape and the reaction container described later is mounted thereon with the undersurface thereof exposed. The movable carriage 43 is configured to be able to move above the temperature controlling unit 41 along a rail 46 set up on the top face of the gene amplifying apparatus 42 by a moving unit 45 composed of a publicly known configuration such as a stepping motor and a servo motor.

In addition to the above configuration, the moving unit 45 can be used by appropriately selecting from configurations of publicly known moving units, for example, a combination of a stepping motor and a belt or a configuration in which the rail 46 and the movable carriage 43 are moved in a non-contact fashion by using a magnetic force or the like.

The measuring unit 44 is constituted by an emission detection unit 47 that introduces excitation light and measures fluorescence and a measuring unit moving unit 48 that moves the emission detection unit 47, and carries out an inspection of a gene sample after being amplified. The measuring unit 44 is not indispensable for the gene amplifying apparatus 42 in the present invention and may not be provided if the configuration is intended for amplification only.

The temperature controlling unit 41 is constituted by a first unit 49 arranged above the movable carriage 43 and a second unit 50 arranged below the movable carriage 43. The first unit 49 is vertically movably supported by a pair of support arms 51. The second unit 50 is also vertically movably supported by a moving unit (not shown).

With the above configuration, the temperature controlling unit 41 is configured so that the first unit 49 and the second unit 50 moves toward the movable carriage 43 stopped between the first unit 49 and the second unit 50 by moving on the rail 46 to be able to sandwich the movable carriage 43 and the reaction container placed on the movable carriage 43 for heating/cooling.

Figure 13:
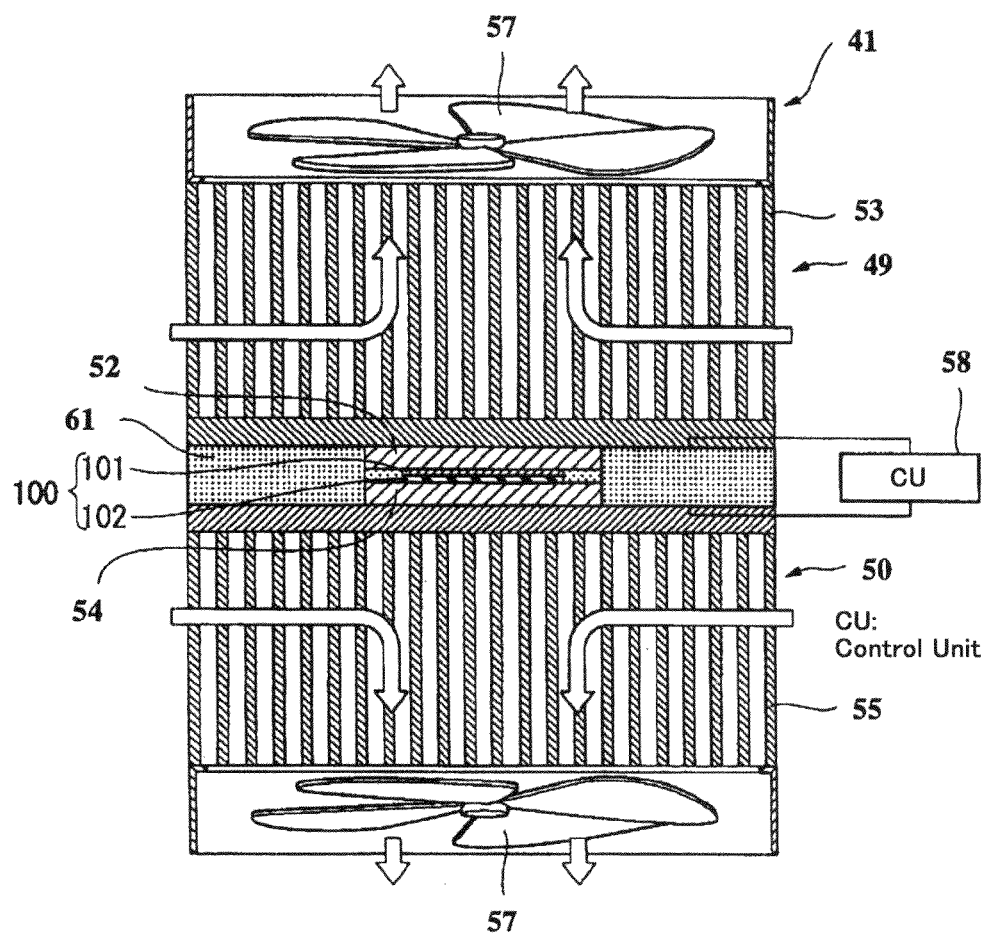
FIG. 13 is a schematic sectional view showing a state where a reaction container is sandwiched by the temperature controlling unit for gene amplifying apparatus.
Figure 14:
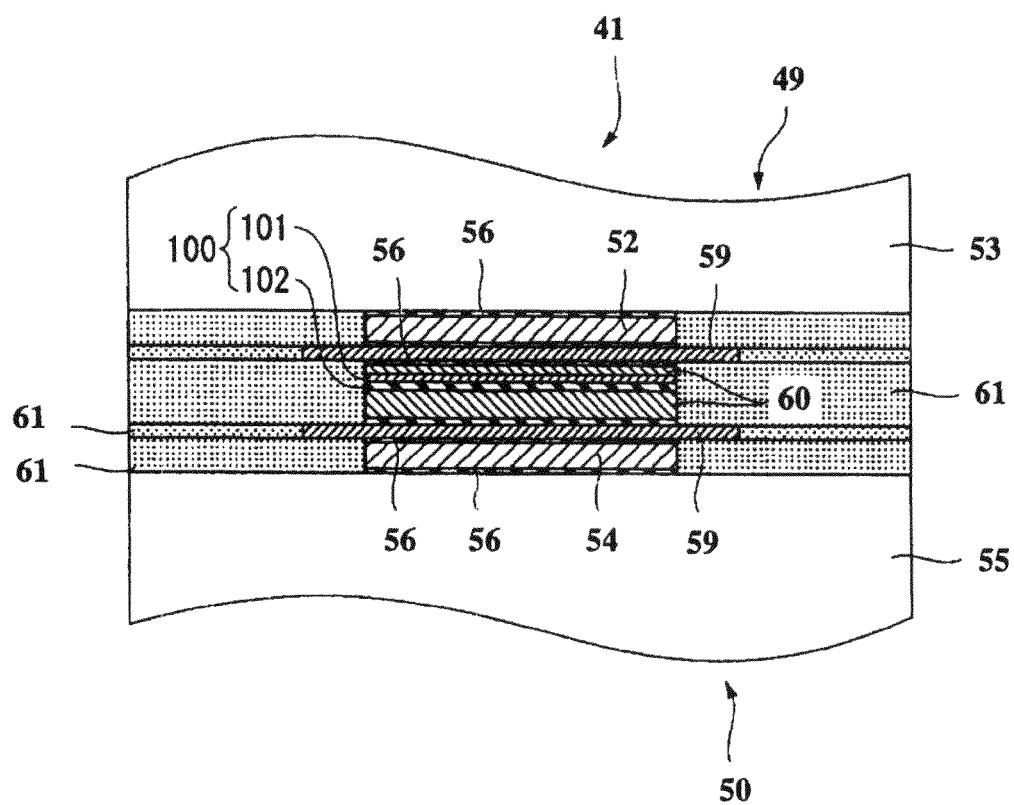
FIG. 14 is an enlarged sectional view in the vicinity of the reaction container in FIG. 13.

FIG. 13 is a schematic sectional view showing a state where a reaction container 100 is sandwiched by the temperature controlling unit 41 and FIG. 14 is an enlarged sectional view showing details near the reaction container 100 in FIG. 13. In FIGS. 13 and 14, units such as the movable carriage 43 and the rail 46 are omitted to make the configuration of the temperature controlling unit 41 easier to understand.

As shown in FIG. 13, the first unit 49 includes a first temperature controlling unit 52 that heats/cools the top face side of the reaction container 100 and a first heat sink (first heat dissipation unit) 53 provided above the first temperature controlling unit 52 in contact with the first temperature controlling unit 52. Similarly, the second unit 50 includes a second temperature controlling unit 54 that heats/cools the undersurface of the reaction container 100 and a second heat sink (second heat dissipation unit) 55, and the first unit 49 and the second unit 50 have the temperature controlling units 52, 54 arranged opposite to each other respectively.

Each of the temperature controlling units 52, 54 is composed of a Peltier module and heats/cools the reaction container 100 by being energized by a power supply (not shown). As shown in FIG. 14, each of the temperature controlling units 52, 54 has a first heat conduction layer 56 made of carbon graphite to improve thermal conductivity provided on upper and lower sides thereof.

Each of the heat sinks 53, 55 is a publicly known air-cooled heat sink closely provided with a fan 57 and dissipates heat generated by each of the temperature controlling units 52, 54 out of the apparatus. Instead of an air-cooled heat sink, a water-cooled heat sink may be provided.

Each of the units 49, 50 is connected to a control unit 58 that sets and controls the temperature each of the temperature controlling units 52, 54. The control unit 58 may be embedded in the gene amplifying apparatus 42 or accommodated in a device such as an external personal computer connected to the gene amplifying apparatus 42. The mode of temperature control of the control unit 58 will be described later.

As shown in FIG. 14, a pair of metallic plates 59 to uniformly dissipate heat generated by each of the temperature controlling units 52, 54 in a surface direction are arranged on the first heat conduction layer 56 on the side of each of the temperature controlling units 52, 54 in contact with the reaction container 100. Silver, aluminum or the like can be adopted as the material of the metallic plate 59.

The above first heat conduction layer 56 is provided on the side of the metallic plate 59 facing the reaction container 100 and a pair of second heat conduction layers (heat conduction members) 60 made of thermal conductive material having elasticity. A silicon rubber sheet (trade name: Sarcon, manufactured by Fuji Polymer) having a high thermal conductivity, a silicone gel sheet (trade name: λGEL, manufactured by Geltec) having a high thermal conductivity or the like can be adopted as the sheet material constituting the second heat conduction layer 60.

The second heat conduction layer 60 mounted on the second unit 50 is preferably made thicker slightly so that the second heat conduction layer 60 is able to be in contact with the entire surface of the reaction container 100 even if the lower part of the reaction container 100 is uneven. In the present embodiment, the thickness of the second heat conduction layer 60 mounted on the first unit 49 to 0.5 mm and that of the second unit 50 to 2.0 mm. If the upper part of the reaction container 100 is uneven, countermeasures can be taken by making the second heat conduction layer 60 mounted on the first unit 49 thicker.

With the above configuration, each of the temperature controlling units 52, 54 heats and cools the entire top face and undersurface of the reaction container 100 via the first heat conduction layer 56, the metallic plates 59, and the second heat conduction layer 60.

Outer circumferences of each of the temperature controlling units 52, 54 and the reaction container 100 are covered with a heat insulating material 61. Resin, Styrofoam or the like can be adopted as the heat insulating material 61.

Figure 15:
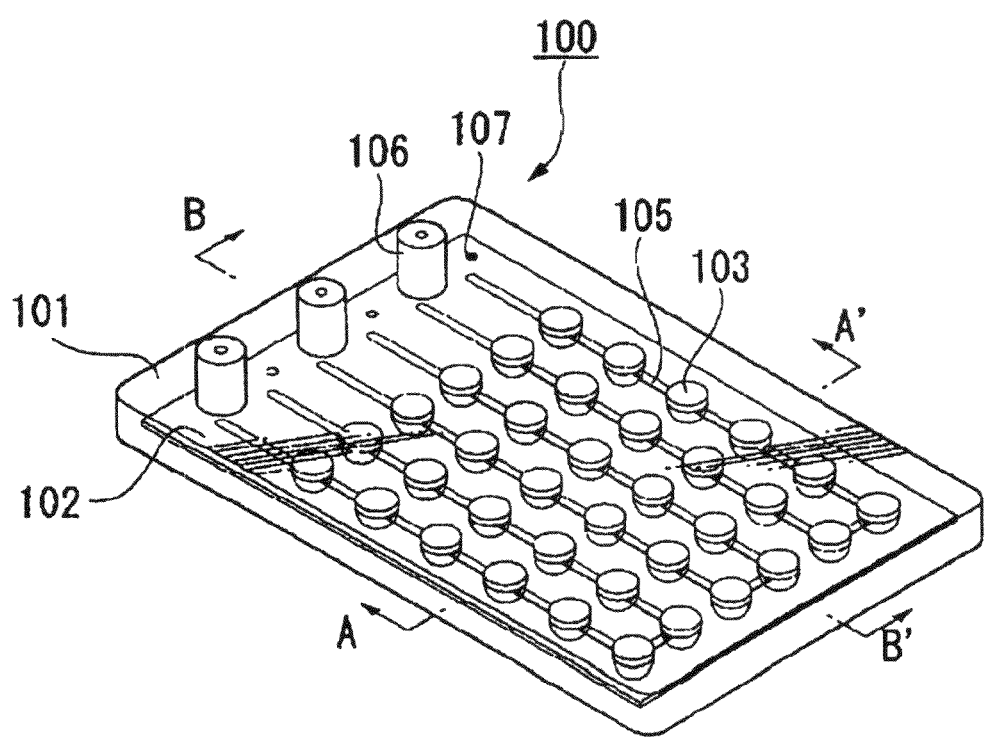
FIG. 15 is a perspective view showing the reaction container.
Figure 16:
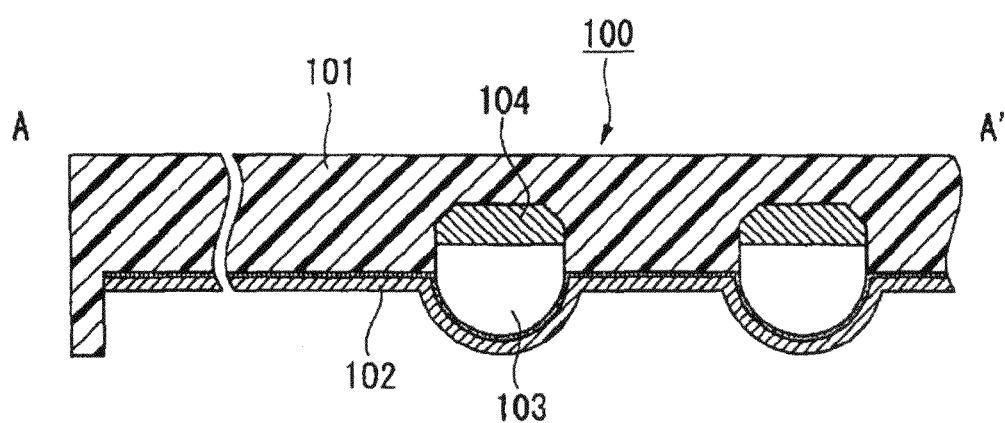
FIG. 16 is a sectional view along a line A-A' in FIG. 15.
Figure 17:
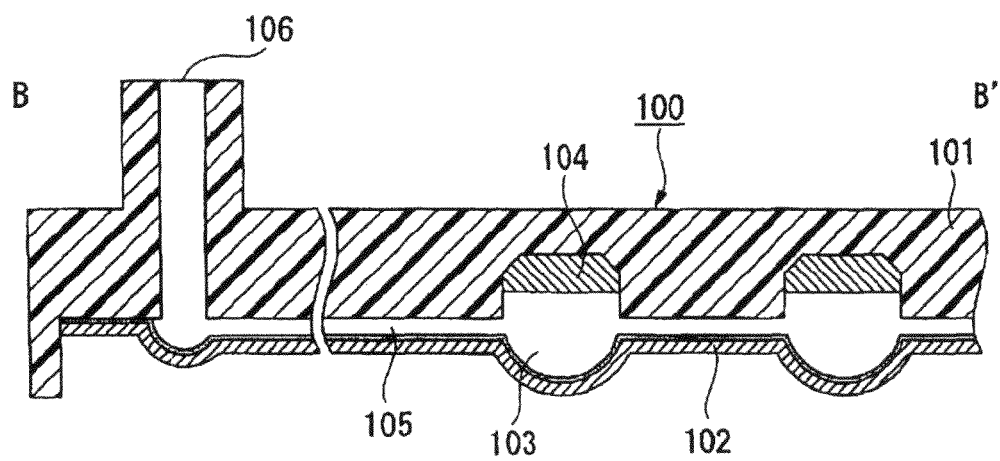
FIG. 17 is a sectional view along a line B-B' in FIG. 15.

FIG. 15 is a perspective view exemplifying the reaction container 100 used in the gene amplifying apparatus 42, FIG. 16 is a sectional view along a line A-A' in FIG. 15, and FIG. 17 is a sectional view along a line B-B' in FIG. 15.

As shown in FIGS. 15 and 16, the reaction container 100 is constituted by a first member 101 made of resin and arranged in the upper part and a second member 102 made of metal and arranged in the lower part.

Polypropylene or the like can be adopted as the first member 101 and aluminum, copper or the like can be adopted as the second member 102.

As shown in FIG. 15, the reaction container 100 has a plurality of wells 103 filled with a gene sample containing genes (nucleic acid). That is, the upper part of each of the wells 103 is formed of the first member 101 and the lower part thereof is formed of the second member 102 and thus, thermal conductivity is different in the upper part and the lower part of each of the wells 103, with the upper part having a lower thermal conductivity.

A reagent 104 used for PCR reaction is arranged on the inner surface of the first member constituting the upper part of the well 103. Incidentally, instead of the reagent 104 being arranged inside the well, the well may be filled with the reagent 104 together with a gene sample described later.

As shown in FIGS. 15 and 17, the wells 103 are communicatively connected by a channel 105 in groups of any number and a injecting hole 106 to inject a gene sample and a deaeration port 107 are provided at both ends of each of the channels 105. When a gene sample is injected through the injecting hole 106, the air inside the channel 105 is exhausted through the deaeration port 107, and the gene sample passes through the channel 105 before each of the communicatively connected wells 103 being filled therewith.

The operation when the gene amplifying apparatus 42 configured as described above is used will be described below.

First, the channel 105 of the reaction container 100 filled with a gene sample is by a jig or the like to make each of the wells 103 an independent space. Then, the reaction container 100 is placed on the movable carriage 43 and the gene amplifying apparatus 42 is started.

The reaction container 100 on the movable carriage 43 is moved on the rail 46 by the moving unit 45 before being stopped between the first unit 49 and the second unit 50 of the temperature controlling unit 41. After the movable carriage 43 being stopped, the first unit 49 falls and the second unit 50 rises before the reaction container 100 being sandwiched from above and from below by the temperature controlling unit 41 so that the first unit 49 and the second unit 50 comes into contact with the entire top face and undersurface of the reaction container 100 respectively.

After the reaction container 100 being sandwiched by the temperature controlling unit 41, the first temperature controlling unit 52 and the second temperature controlling unit 54 are energized by a power supply (not shown). Then, the reaction container 100 is heated and cooled to reach a predetermined temperature cycle under the control of the control unit 58 to amplify a gene contained in the gene sample inside the reaction container 100 by the PCR method.

Figure 18:
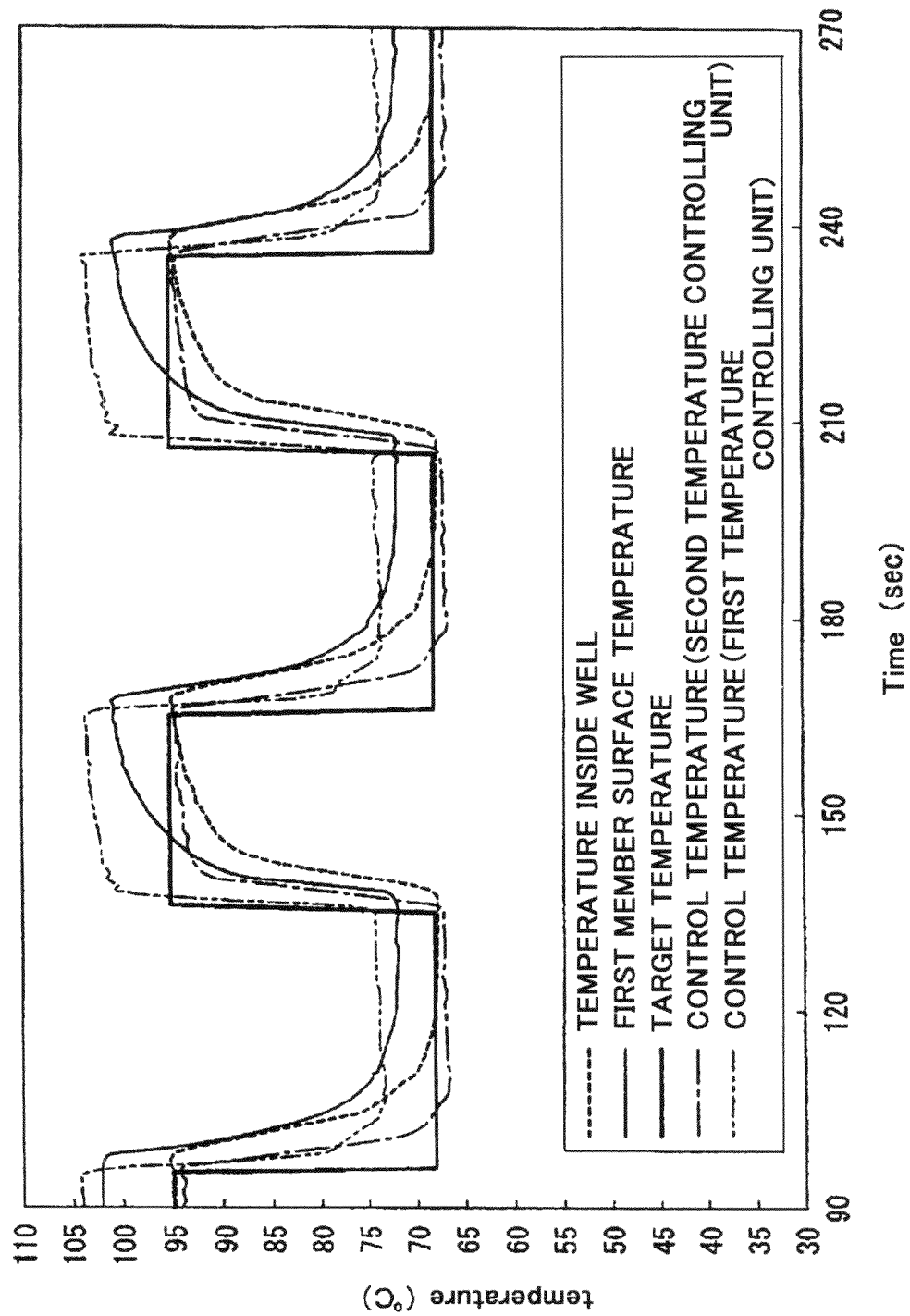
FIG. 18 is a graph showing a temperature cycle by the PCR method, temperature control by the temperature controlling unit for gene amplifying apparatus, and temperature changes of each unit of the reaction container.

FIG. 18 is a graph showing a temperature cycle by the PCR method, temperature control by the temperature controlling unit 41, and temperatures of each unit of the reaction container. The control unit 58 exercises independent temperature control for the first temperature controlling unit 52 and the second temperature controlling unit 54.

In the present embodiment, as shown in FIG. 18, gene amplification by the PCR method is carried out, as indicated by a thick solid line, in a temperature cycle in which temperatures near 95° and 68° are mutually repeated. Therefore, this temperature cycle becomes a target temperature for the gene sample and the reference for temperature control by each of the temperature controlling units 52, 54.

The lower part of the reaction container 100 is formed of the second member 102 having a high thermal conductivity and thus, by heating the second temperature controlling unit 54, as indicated by an alternate long and short dash line, up to about 95° C., the temperature inside the well 103 (near the central part in the vertical direction) also rises, as indicated by a broken line, up to close to 95° C. However, the upper part of the reaction container 100 is formed of the first member 101 whose thermal conductivity is lower than that of the second member 102 and therefore, the temperature of the gene sample near the first member 101 may not rise up to close to 95° C. necessary for PCR reaction. In such a case, the PCR reaction may not proceed or proceeds only insufficiently.

Thus, as indicated by a chain double-dashed line, the preset temperature of the first temperature controlling unit 52 is set to about 105° C., which is higher than the target temperature 95° C. Accordingly, as indicated by a thin solid line, the surface temperature of the first member 101 rises to 95° C. or higher so that it is supposed that the temperature inside the well 103 becomes uniform as a whole and also the fact that temperature changes proceed quickly along the preset temperature cycle was confirmed.

Actually, with the above temperature settings, the PCR reaction inside the reaction container 100 proceeded satisfactorily so that 35 cycles could be completed in about 41 minutes, which is about half the time that was needed with a conventional apparatus.

Figure 19:
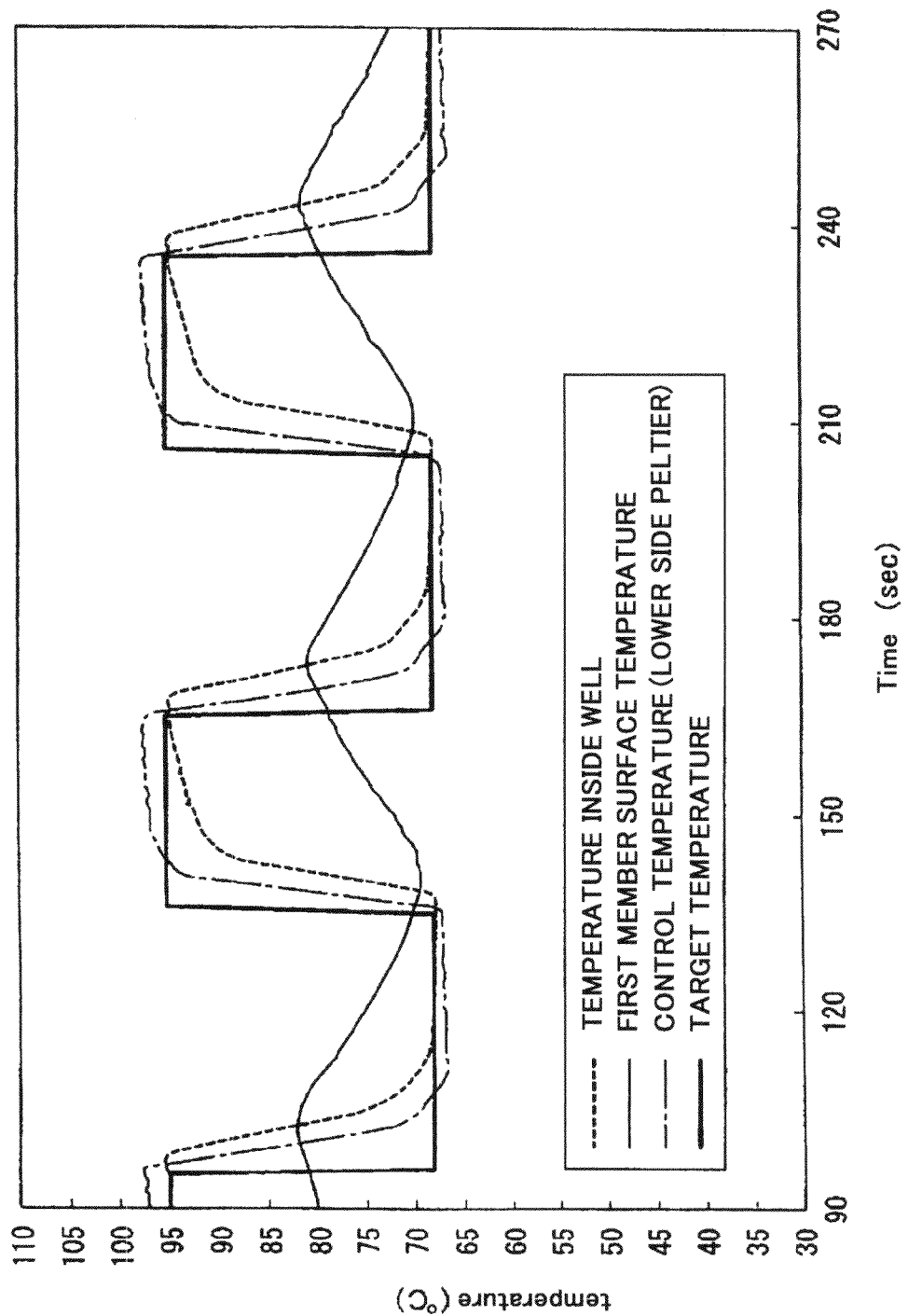
FIG. 19 is a graph showing temperature changes when the reaction container 100 is used in a conventional gene amplifying apparatus.

FIG. 19 is a graph showing, as an example of a conventional apparatus, temperature changes when the reaction container 100 is used in a gene amplifying apparatus that heats/cools the reaction container 100 by a Peltier module being brought into contact with only the lower part thereof. While the temperature inside the well rises up to close to 95° C. by the Peltier module, the surface temperature of the first member 101 rises only to close to 80° C. so that it is supposed that the temperature inside the well is non-uniform. Actually, cases where the PCR reaction did not proceed in this gene amplifying apparatus were confirmed.

In this apparatus, it seems that quite a long time will be needed to bring the surface temperature of the first member 101 closer to the target temperature as far as a temperature profile is concerned and it is assumed that the total time necessary for PCR reaction will be very long.

On the other hand, even if an attempt is made to reduce the PCR time by rapid heating and rapid cooling by setting the control temperature of the Peltier module higher than the target temperature when the temperature rises and lower when the temperature falls, a region where the temperature inside the well (particularly near the lower part) follows behavior of the control temperature arises because the undersurface of the reaction container 100 is composed of the second member 102 having a high thermal conductivity so that a case where the reagent inside the well is devitalized can be considered.

Actually, a case where the PCR reaction did not proceed when such control was exercised is confirmed and devitalization of the reagent was suggested as one of possible causes why the PCR reaction did not proceed.

The temperature control of the temperature controlling unit 41 by the control unit 58 described above is only an example and setting parameters such as the actual preset temperature and lengths of the heating/cooling time (the time during which the preset temperature is maintained) are independently decided for the first temperature controlling unit 52 and the second temperature controlling unit 54 depending on reaction container parameters such as the thermal conductivity, thickness and the like for each material of the first member 101 and the second member 102.

Thus, not only the preset temperature, but also the heating/cooling time may be different for the first temperature controlling unit 52 and the second temperature controlling unit 54. Therefore, setting parameters for each reaction container parameter may be stored in the control unit 58 as a table in advance so that, based on user input or the like, the control unit 58 exercises temperature control of the first temperature controlling unit 52 and the second temperature controlling unit 54 by referring to corresponding setting parameters in the table when appropriate.

The reaction container 100 whose amplification is completed moves up to the measuring unit 44 along the rail 46. Then, various measurements such as fluorescence intensity of the sample in each of the wells 103 are made by the measuring unit 44. A sample amplified by the gene amplifying apparatus 42 of the present invention can be offered to various genetic tests such as a base sequence test of a gene, polymorphism test based on a repetitive sequence with a certain base sequence set as a unit, and test of single nucleotide polymorphism (SNPs or SNP).

According to the temperature controlling unit 41 and the gene amplifying apparatus 42 in the present embodiment, heat generated by the first temperature controlling unit 52 and the second temperature controlling unit 54 is efficiently transmitted to the reaction container 100 by the first heat conduction layer 56, the metallic plates 59, and the second heat conduction layer 60. Thus, even if the reaction container 100 is formed by including the first member 101 and the second member 102 having different thermal conductivities, a filled gene sample is appropriately heated/cooled and a time required to realize a temperature cycle necessary for the PCR method is reduced so that the gene can be amplified quickly and suitably.

Moreover, the control unit 58 exercises temperature control of the first temperature controlling unit 52 and the second temperature controlling unit 54 independently in accordance with various parameters including thermal conductivities of the members 101, 102 of the reaction container 100 so that each of the first temperature controlling unit 52 and the second temperature controlling unit 54 is controlled to the optimum preset temperatures and heating/cooling times to set the gene sample at temperatures in keeping with the temperature cycle of PCR. Therefore, the gene sample filled inside the reaction container 100 can be PCR-treated more suitably.

Moreover, the circumference of each of the temperature controlling units 52, 54 sandwiching the reaction container 100 is covered with the heat insulating material 61 and thus, heat exchanged between each of the temperature controlling units 52, 54 and the reaction container 100 does not escape to the outside so that the temperature of the reaction container 100 can be controlled more efficiently.

Further, the first heat sink 53 and the second heat sink 55 are provided in contact with the first temperature controlling unit 52 and the second temperature controlling unit 54 respectively and thus, when the reaction container 100 is cooled, heat transmitted to each of the temperature controlling units 52, 54 can efficiently be dissipated out of the temperature controlling unit 41.

In the foregoing, an embodiment of the present invention has been described, but the technical scope of the present invention is not limited to the above embodiment and various modifications can be made without deviating from the spirit of the present invention.

For example, an example in which the first heat conduction layer 56 is provided in contact with each of the temperature controlling units 52, 54 and the metallic plates 59 is described in the above embodiment, but the arrangement position of the first heat conduction layer 56 is not limited to this. Other examples may include providing the first heat conduction layer 56 in contact with only each of the temperature controlling units 52, 54 and in contact with only the metallic plates 59.

Moreover, if the temperature is controlled satisfactorily, the first heat conduction layer 56 need not necessarily be provided.

The reaction container to be used is not limited to, as described above, a reaction container in which the thermal conductivity of the upper part is lower than that of the lower part and, for example, a reaction container in which the thermal conductivity of the upper part is higher than that of the lower part may also be adopted. In such a case, the PCR reaction can be caused to proceed more suitably by changing the control mode of the control unit.

In a temperature controlling unit and a gene treating apparatus of the present invention, the control unit is not required. For example, if the difference in thermal conductivity between first and second members is relatively small and the PCR reaction can be caused to proceed without independent temperature control of first and second temperature controlling units, the temperature controlling unit and the gene treating apparatus may be configured without providing a control unit.

Further, units such as a movable carriage and a rail to move a reaction container are not required in a gene treating apparatus of the present invention. For example, the gene treating apparatus may be configured in such a way a reaction container is directly set up between the first unit 49 and the second unit 50 by the user and the temperature is controlled for PCR reaction at the setup position.

In addition to an amplification reaction by the PCR method, a temperature controlling unit and a gene treating apparatus of the present invention can also be used when a predetermined temperature is maintained for a fixed time like, for example, a reaction by the invader method. In such a case, the temperature of a gene sample in a reaction container can suitably be controlled without being affected by a difference in thermal conductivity of members constituting the reaction container.

According to a reaction chip of the present invention, a notch showing a gradual increase in width and a gradual increase in depth from one face of the base material toward an inner wall surface of the recess is formed on an edge of at least one recess of the recesses in an extending direction of the groove and therefore, the flow of a reagent solution becomes smooth near the recess so that the reagent solution smoothly flows into the recess constituting a reaction container from a groove constituting a channel or flows out to the groove from the recess. Thus, even a reagent solution containing bubbles comes flowing, the frequency with which bubbles remain inside the recess by being entrapped by the inner wall surface of the recess can significantly be decreased. Therefore, the desired reaction can accurately be detected and measured by using a reaction chip of the present invention. Moreover, bubbles can be removed from inside the recess simply by molding a notch on an edge of the recess and therefore, there is no need of hydrophobic/hydrophilic treatment and surface treatment such as corona treatment and plasma treatment.

If the configuration is adopted in which the angle formed by one face of the base material and the notch is smaller than that formed by one face of the base material and the inner wall surface of the recess, the inclination of the inner wall surface on the inflow side or outflow side of the recess becomes gentle, which makes the flow of the reagent solution in a sectional direction of the base material smooth, so that bubbles can effectively be prevented from remaining.

If a notch is formed only on one side of the extending direction of the groove and the configuration is adopted in which the notch is formed on the inflow side of the reagent solution, the reagent solution flows into the recess from the groove smoothly so that bubbles can effectively be prevented from remaining.

If a notch is formed also on the outflow side of the reagent solution and the configuration in which the notch formed on the inflow side of the reagent solution and the notch formed on the outflow side of the reagent solution form a line symmetric shape is adopted, two notches can be formed easily and also the flow of the reagent solution becomes smooth, so that bubbles can more effectively be prevented from remaining.

If the recess has a columnar space having the inner wall surface at substantially right angles to one face of the base material on an opening side and the maximum depth on the edge of the notch is shallower than the depth of the columnar space, the inner wall surface at substantially right angles in the columnar space will remain on the edge of the recess on the side on which the notch is formed. By using this inner wall surface, a reagent or a fixing agent that temporarily fixes the reagent can reliably be accommodated, so that reaction products can be prevented from leaking to adjacent reaction containers.

If an outer shape of the recess is circular in plane view and the configuration is adopted in which a plane shape of the notch is defined, when two tangents to a circle forming an outer edge of the recess are drawn from one point on one face of the base material in the extending direction of the groove, by an area inside the two tangents, an overall shape of the recess including the notch has a shape with the least flow resistance and the flow of the reagent solution near the recess becomes extremely smooth, so that bubbles can more reliably be prevented from remaining.

If a center line in the extending direction of the groove of the notch is aligned with the center line of the groove on the same straight line, the flow of the reagent solution becomes smooth without being deviated inside the recess, so that bubbles can more reliably be prevented from remaining.

According to a reaction method of the present invention, a reaction chip is constituted by a first base material with a relatively low thermal conductivity, and a second base material with a relatively high thermal conductivity and a reagent is arranged inside a recess of the first base material. Then, when a reaction is caused, heat is added from the side of the second base material with a higher thermal conductivity and the reagent and a reagent solution are brought into contact by melting a sealing compound to cause the reaction to proceed. Therefore, when the reagent solution is fed, the reagent is covered with the sealing compound so that contamination can be prevented from occurring. While thermal efficiency for the whole reaction container is excellent by adding heat from the side of the second base material, the reagent is arranged on the side of the first base material with a lower thermal conductivity and therefore, it is hard for heat added during chip manufacturing to be transmitted to the reagent so that activity of the reagent will be neither lowered nor devitalized. Accordingly, accurate reaction data can be measured.

If the configuration in which heat is added from the side of the second base material and the first base material and the second base material are stuck together by thermal welding of a sealant layer provided on at least one of the first base material and the second base material is adopted, it is hard for the sealing compound to melt by heat when the base materials are stuck together, malfunctions such as blockage of the channel due to outflow of the sealing compound and incomplete sealing of the reagent can be prevented so that a reaction chip can be produced with stability and also contamination can reliably be prevented from occurring. If a sealant layer that does not inhibit a reaction is used, the material of each base material can freely be selected. Accordingly, the material capable of realizing a chip having high heat resistance, barrier property, chemical resistance, and reagent preservability and superior in reactivity (thermal conductivity) can be selected.

If a recess corresponding to the recess of the first base material is formed also on the second base material to configure the reaction container by both the recess of the first base material and that of the second base material, a sufficient volume of the reaction container can be ensured and also flexibility of design for the volume and shape of the reaction container can be increased. Moreover, the surface area of the second base material with a higher thermal conductivity increases, which increases the thermal conductivity for the whole reaction container, so that a reaction that proceeds by heating such as an enzyme reaction can be caused more efficiently in a short time.

If the configuration in which a resin material is used as the first base material and a metallic material is used as the second base material is adopted, a reaction container or channel having the above excellent characteristics can easily be worked on.

If the sealing compound is constituted by a material soluble in neither a reagent nor a reagent solution, the reagent and the reagent solution can come into contact and react without any change in composition thereof so that accurate reaction data can be measured.

If the reaction container is a reaction container for enzyme reaction, a DNA amplification reaction by an enzyme reaction, DNA detection reaction by hybridization, and detection reaction of SNP, which are general biochemical reactions, can be realized on a reaction chip.

According to a temperature controlling unit for gene treating apparatus and a gene treating apparatus of the present invention, even if a reaction container constituted by plural types of materials having different thermal conductivities, a gene contained in a gene sample filled in the reaction container can suitably be treated.

EXAMPLES

The present inventors carried out experiments below to demonstrate effects of the first embodiment of the present invention.

Example 1

First, the resin base material 2 including the recess 6 having the shape and layout shown in FIGS. 2 and 4 according to the above embodiments is produced by injection molding. Polypropylene determined not to inhibit a reaction is used as a material. As for the notch 15, after the resin base material 2 including the recess 6 being produced by using injection molding, the notch 15 is formed by cutting at upstream and downstream positions of the channel 5 on the edge of the recess 6. On the other hand, what is produced by performing drawing on an aluminum original sheet to which a polypropylene sealant is applied is used as the metallic base material 3 with the intention of improving thermal efficiency during reaction.

While the reaction chip has a reagent arranged in each of the reaction containers 4 in a normal case, the present experiment is intended to check the state of bubbles during feeding and thus, instead of a reagent, 5 µl of AmpliWax (trade name, manufactured by ABI) is each put into the recess 6 of the resin base material 2. The resin base material 2 having AmpliWax arranged inside the recess 6 and the metallic base material 3 are welded by thermal welding to produce a reaction chip in the present embodiment.

Comparative Example 1

Figure 20A:
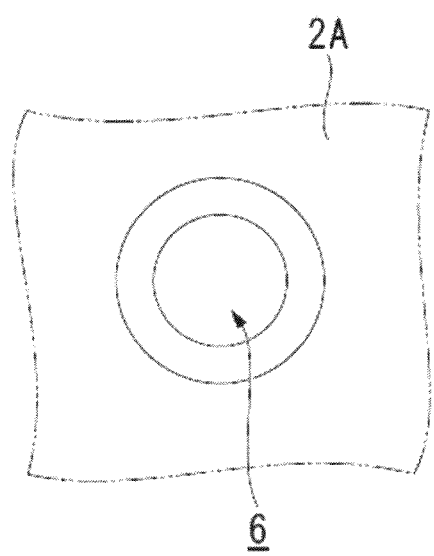
FIG. 20A is a plan view thereof and FIG. 20B is a side sectional view thereof.
Figure 20B:
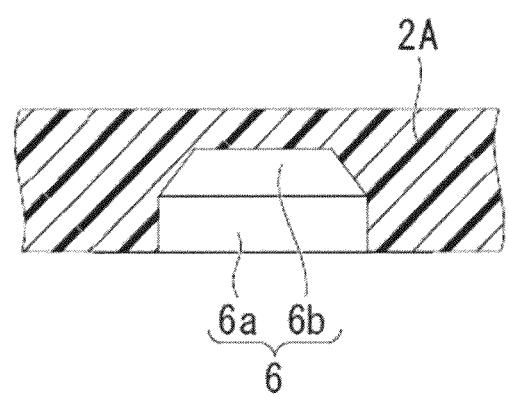
Figure 21A:
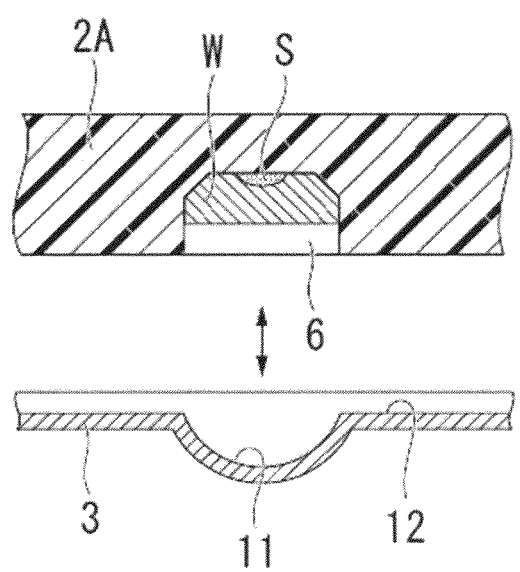
FIGS. 21A, 21B and 21C are process sectional views when the reaction chip of Comparative Example 1 is used.
Figure 21B:
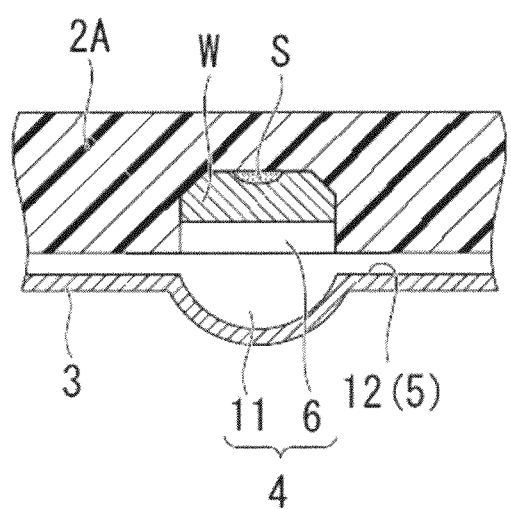

A resin base material 2A including the recess 6 having no notch as shown in FIGS. 20A and 20B is produced and then, a reaction chip of Comparative Example 1 is produced by following the same method as that of Example 1 described above (see FIGS. 21A and 21B).

As reagent solutions to be fed, a reagent solution A obtained by diluting a PCR product 10 times and a reagent solution B composed of a 10 mg/ml protein solution (BSA solution) are prepared. These reagent solutions A and B are fed to three reaction chips each for Example 1 and Comparative Example 1 by an electric pipette (Finnpipette Novus 30-300 µl (trade name), manufactured by Thermo Fisher Scientific) at the flow rate of 200 µl/21 sec.

Figure 22:
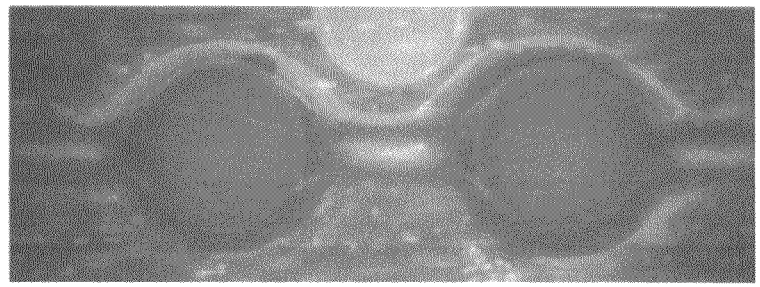
FIG. 22 is a photo shooting conditions inside the reaction container of the reaction chip of Example 1.

If a reagent solution is fed, bubbles contained in the reagent solution are introduced into each reaction container, but in reaction chips of Example 1, bubbles once introduced flow out together with the reagent solution and no bubble remains inside the reaction container. FIG. 22 shows a photo shooting conditions inside the reaction container through a transparent resin base material.

Figure 21C:
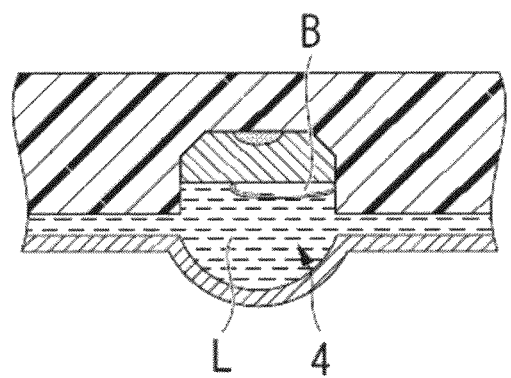
Figure 23:
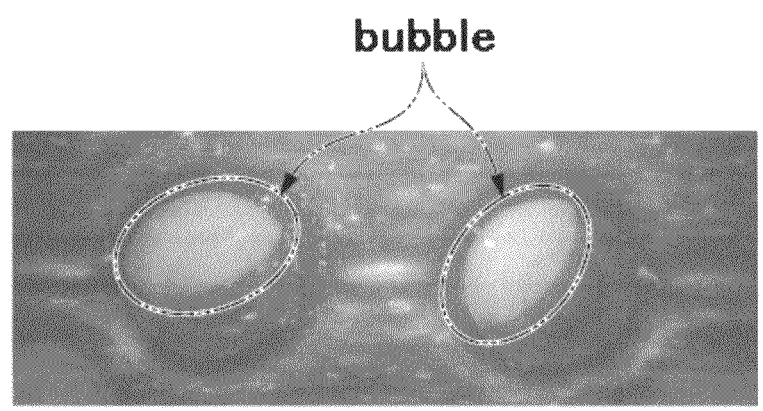
FIG. 23 is a photo shooting conditions inside the reaction container of the reaction chip of Comparative Example 1.

In reaction chips of Comparative Example 1, on the other hand, bubbles once introduced do not flow out of the reaction container and, as shown in FIG. 21C, a bubble B remaining inside the reaction container 4 is observed. FIG. 23 shows a photo shooting conditions inside the reaction container.

Numbers of reaction containers in which bubbles remain during feeding in each of reaction chips of Example 1 and Comparative Example 1 are listed in [Table 1]. The total number of reaction containers is 108 because three reaction chips each with 36 reaction containers are fed. While the number of reaction containers in which bubbles remain is 0 for both the reagent solution A and the reagent solution B in reaction chips of Example 1, the number of reaction containers in which bubbles remain is 8 for the reagent solution A and 18 for the reagent solution B in reaction chips of Comparative Example 1.

TABLE 1

|  | Reaction container shape | Reagent solution A PCR diluted solution | Reagent solution B Protein solution |
|---|---|---|---|
| Example 1 | With notch | 0 | 0 |
| Comparative Example 1 | Without notch | 8 | 18 |

From the above result, an effect of the reaction chip of the present invention having a recess with notch is proved.

Figure 24A:
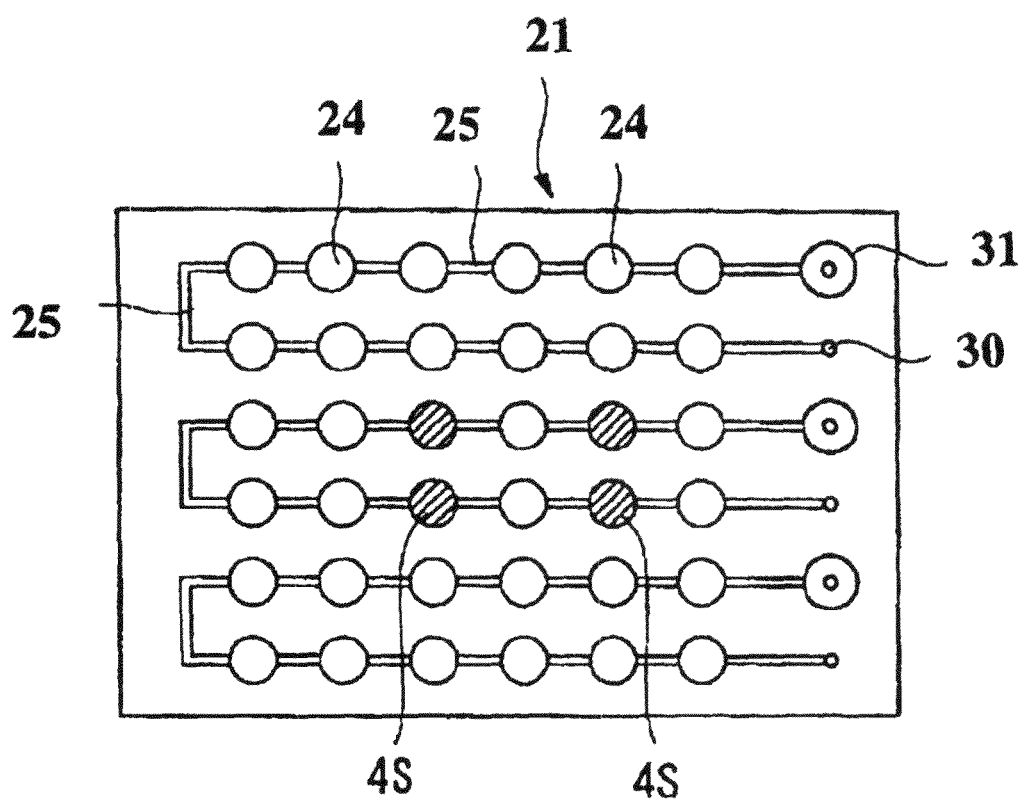
FIG. 24A is a plan view showing reagent arrangement of Example 2 and Comparative Example 2 of the present invention.
Figure 24B:
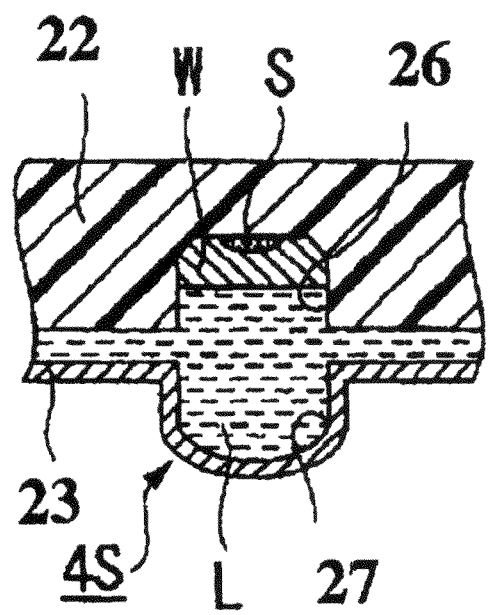
FIG. 24B is a sectional view of the reaction chip of Example 2.
Figure 24C:
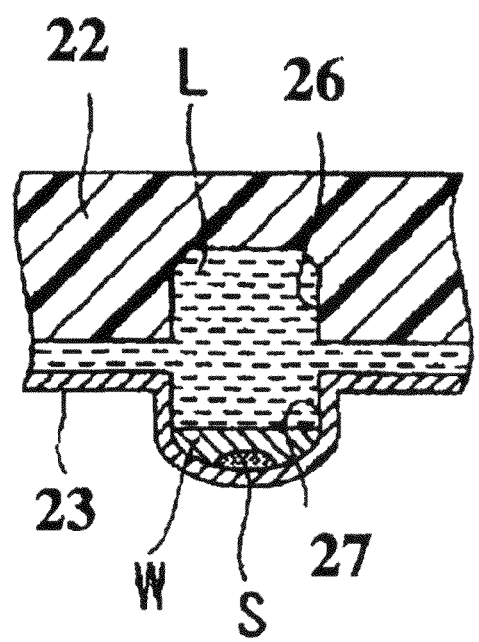
FIG. 24C is a sectional view of the reaction chip of Comparative Example 2.

The detection method of SNP using the invader (registered trademark) method executed by the present inventors as Example 2 of a reaction chip and a reaction method according to the second embodiment of the present invention will be described below. FIG. 24A is a plan view showing reagent arrangement of Example 2 and Comparative Example 2, FIG. 24B is a sectional view of the reaction chip of Example 2, and FIG. 24C is a sectional view of the reaction chip of and Comparative Example 2.

Example 2

As shown in FIG. 24A, a reaction chip described in the above embodiment is produced. The cover material 22 is produced by the method of injection-molding polypropylene resin inside a die and a plurality of recesses 26 and a plurality of reagent solution injecting holes 30 are formed on a resin base material with a thickness of 2 mm. The opening diameter of the recess 26 is 3 mm, the diameter thereof at the bottom is 2 mm, and the depth thereof is 1.5 mm. The volume of the recess 26 is theoretically about 9 μl and the distance between the adjacent recesses 26 is 6 mm. The outside diameter of the reagent solution injecting hole 30 is 4 mm and the inside diameter of the hole is 1.5 mm to 2 mm, creating a tapered shape. The height thereof is 6 mm from the top face of the cover material 22.

A material in which a sealant layer made of polypropylene of 70 μm is stacked on an aluminum plate of 0.1 mm via an adhesive is used as the substrate 23 and the channel 25 communicatively connecting the recess 27 and the recess 27 is formed by drawing. The opening diameter of the recess 27 is 3 mm and the depth thereof is 1.5 mm. The volume of the recess 27 is theoretically about 7 μL and the distance between the adjacent recesses 27 is 6 mm. The width of the channel 25 is 1 mm and the depth thereof is 0.3 mm.

As shown in FIG. 24B, the fixing reagent S is arranged in the recess 26 of the cover material 22 corresponding to shaded reaction containers 4S in FIG. 24A. An allele probe 1, an allele probe 2, and an invader probe used for an invader (registered trademark) reaction and an FRET probe 1, an FRET probe 2, and Cleavase (registered trademark) are arranged as the fixing reagents S before heating/drying.

Next, AmpliWax (registered trademark) PCR Gem 100 manufactured by Applied Biosystems is put into all the recesses 26 as the sealing compound W. The amount of the sealing compound W for one recess 26 is 4.5 μL. The sealing compound W is heated to 80 to 100° C. to be dispensed to the recess 26 while being melted and, after a centrifugal operation being performed by a plate centrifuge, the sealing compound W is solidified again at ordinary temperature. Accordingly, the fixing reagent S is covered with the sealing compound W in the shaded reaction containers 4S in FIG. 24A.

Next, the cover material 22 and the substrate 23 produced above are stuck together by a heat seal under the conditions of 250° C., 0.5 MPa, 1.4 s, and one-sided heating from the substrate 23 side using a heat seal tester manufactured by Tester Sangyo.

Next, a mixed solution of a PCR product amplified from purified genome DNA, an invader buffer, and water for dilution thereof is fed as a reaction reagent solution. The reaction reagent solution L is caused to reach all the reaction containers 24 through the channel 25 from the reagent solution injecting hole 30 of the cover material 22. The amount of feeding of the reaction reagent solution L to one reaction container 24 is 12 to 15 μl.

Then, the reaction chip 21 is set to a developed analysis chip dedicated apparatus. In the apparatus, a part of the channel 25 is crushed by an external force for sealing between the reaction containers 24 and 4S so that a reaction liquid during reaction should not be exchanged between the reaction containers 24. At this point, heat is added simultaneously with the external force for thermal welding of the sealant layer of the cover material 22 and the substrate 23 to strengthen sealing. The sealing occurs under the conditions of 190° C., 120 kgf, and 1.5 s.

Next, the reaction chip 21 is heated from the substrate 23 side inside the apparatus to cause a reaction. First, while the sealing compound W is melted under the conditions of 95° C. and 5 minutes to bring the fixing reagent S and the reaction reagent solution L into contact, the PCR product in the reaction reagent solution is altered in quality. Then, the temperature is lowered to 63° C. and a fluorescent substance is detected inside the reaction containers 4S are detected once in every 30 seconds while causing an invader reaction to observe reaction conditions at regular intervals.

Comparative Example 2

The cover material 22 and the substrate 23 are produced in the same manner as the above Example 2. Then, in Comparative Example 2, as shown in FIG. 24C, the fixing reagent S and the sealing compound W are arranged in the recess 27 of the substrate 23. After the cover material 22 and the substrate 23 being stuck together by a heat seal, the reaction reagent solution L is input through the reagent solution injecting hole 30 at ordinary temperature. Next, after being sealed between the reaction containers 24 and 4S in the apparatus, the reaction chip 21 is heated from the substrate 23 side to melt the sealing compound and bring the fixing reagent and a reaction reagent solution into contact and then, a fluorescent substance is detected while an invader reaction being caused.

(Experiment Results)

Figure 25A:
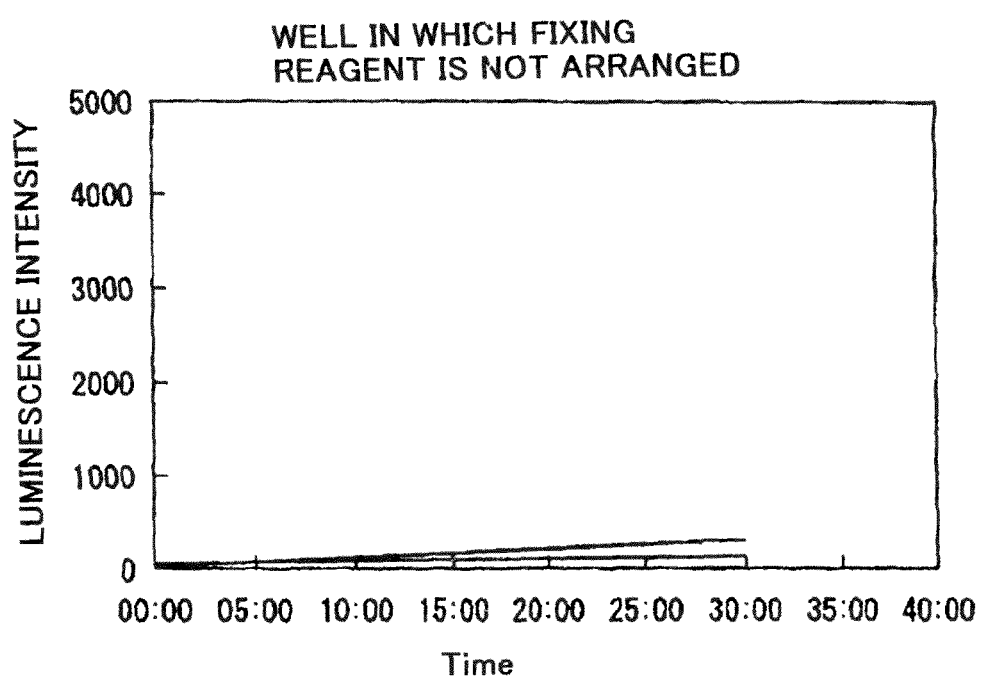
FIGS. 25A and 25B are graphs showing reaction results of Example 2.
Figure 25B:
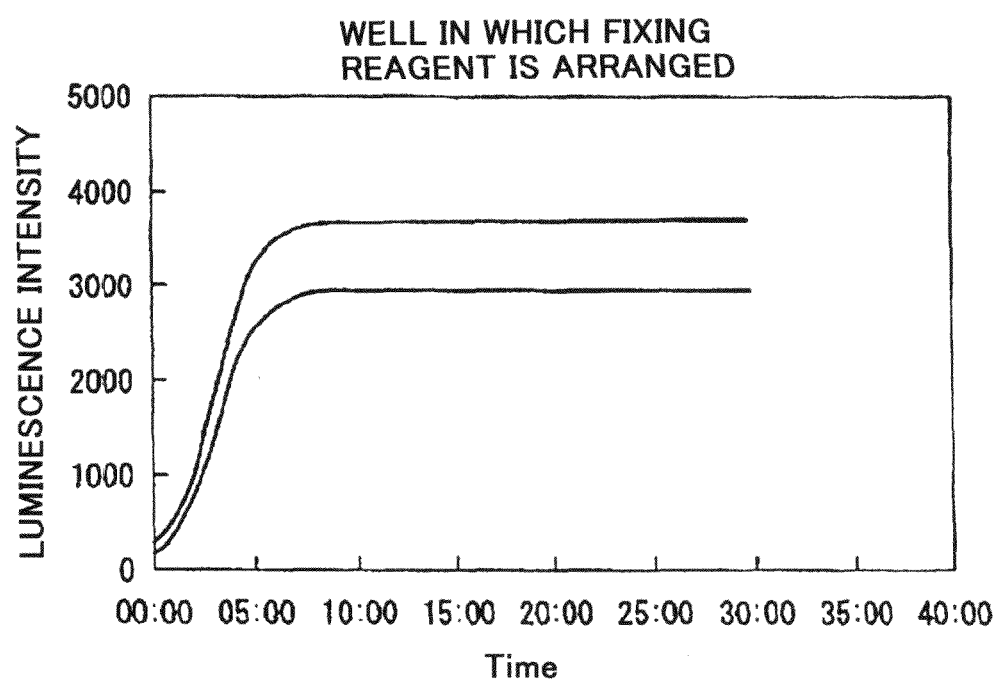

FIGS. 25A and 25B show results of reactions caused in Example 2, and FIG. 25A shows luminescence intensity in an adjacent reaction container of a reaction container in which a fixing reagent is arranged and FIG. 25B shows luminescence intensity in a reaction container in which a fixing reagent is arranged. The horizontal axis of the graph represents a reaction time and the vertical axis thereof represents fluorescence intensity. As is evident from these graphs, only the graph of the reaction container in which the fixing reagent is arranged in FIG. 25B shows that the reaction proceeded without any problems. Moreover, no proceeding reaction is observed in the adjacent reaction container in which no fixing reagent is arranged of the reaction container in which the fixing reagent is arranged, which shows that the fixing reagent can be concealed by the sealing compound without causing any problem.

Figure 26A:
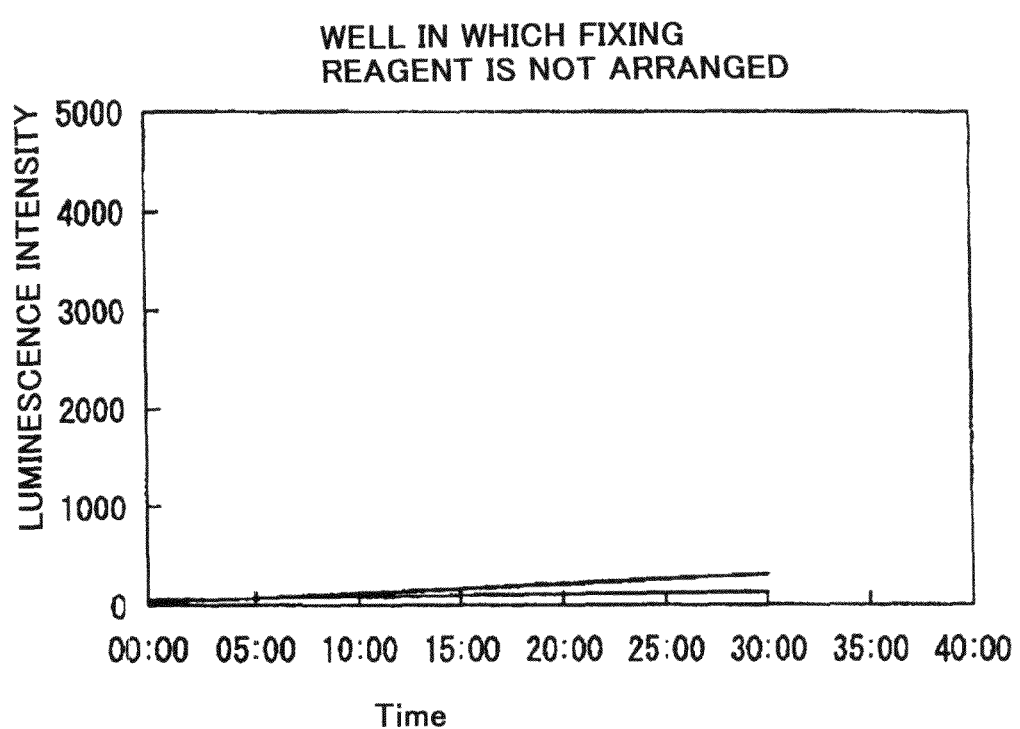
FIG. 26 is a graph showing reaction results of Comparative Example 2.
Figure 26B:
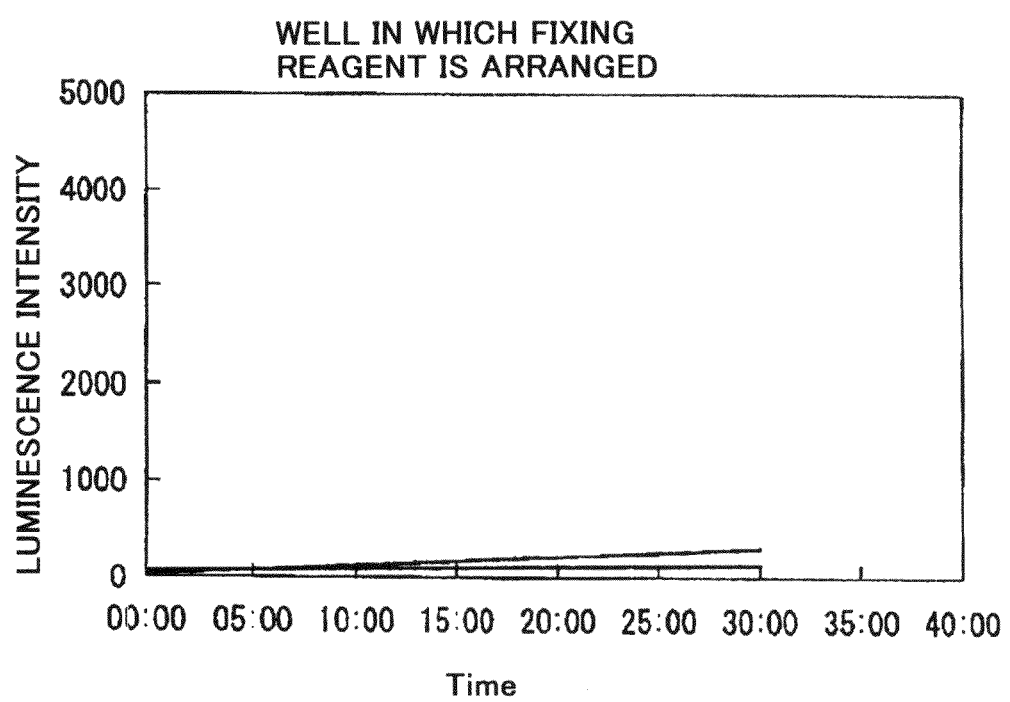

On the other hand, FIGS. 26A and 26B show results of reactions performed in Comparative Example 2, and FIG. 26A shows luminescence intensity in an adjacent reaction container of a reaction container in which a fixing reagent is arranged and FIG. 26B shows luminescence intensity in a reaction container in which a fixing reagent is arranged. These results show that the reaction did not proceed at all in the reaction container in which the fixing reagent is arranged, either. This can be considered that because the fixing reagent S is arranged in the recess 27 on the substrate 23 side having an aluminum plate, heat during heat sealing of the cover material 22 and the substrate 23 is transmitted through aluminum with a high thermal conductivity to add more heat to the fixing reagent S, resulting in lowering or devitalization of activity of the reagent.

The above demonstrates that, according to the reaction method of the present invention, reaction data can be measured accurately without causing lowering or devitalization of activity of a reagent.

The invention claimed is:

1. A temperature controlling assembly for a gene treating apparatus that treats a gene inside a gene sample by heating/cooling the gene sample filled in a reaction container comprising a first member arranged in an upper part and a second member arranged in a lower part, the second member having a different thermal conductivity from that of the first member, the temperature controlling assembly comprising:

a first temperature controlling unit arranged in such a way to allow contact with a top face of the reaction container;

a second temperature controlling unit arranged in such a way to allow contact with an undersurface of the reaction container and also arranged in such a way to be able to sandwich the reaction container between the first temperature controlling unit and the second temperature controlling unit;

a pair of metallic plates arranged on surfaces where the first temperature controlling unit and the second temperature controlling unit is in contact with the reaction container;

a pair of first heat conduction members arranged on surfaces of the pair of metallic plates facing the reaction container and also arranged in such a way to allow contact with the top face and the undersurface of the reaction container;

a pair of second heat conduction members arranged on surfaces of the pair of first heat conduction members facing the reaction container and also arranged in such a way to allow contact with the top face and the undersurface of the reaction container;

a first heat dissipation unit provided in contact with the first temperature controlling unit; and a second heat dissipation unit provided in contact with the second temperature controlling unit wherein one of the pair of second heat conduction members in a side of the undersurface of the reaction container is thicker than another of the pair of second heat conduction members in a side of the top face of the reaction container.

2. The temperature controlling assembly according to claim 1, further comprising a control unit connected to the first temperature controlling unit and the second temperature controlling unit to control temperatures of the first temperature controlling unit and the second temperature controlling unit, wherein the control unit exercises temperature control of the first temperature controlling unit and the second temperature controlling unit independently based on the thermal conductivities of the first member and the second member.

3. A gene treating apparatus, comprising:

the temperature controlling assembly according to claim 1; and an emission detection unit.

* * * * *